US006204029B1

(12) United States Patent
Withers et al.

(10) Patent No.: US 6,204,029 B1
(45) Date of Patent: *Mar. 20, 2001

(54) GLYCOSYLATED ACCEPTOR SYNTHESIS CATALYZED BY GLYCOSYL TRANSFERASE AND NUCLEOTIDE PHOSPHATE SUGAR-DEPENDENT ENZYME

(75) Inventors: Stephen G. Withers; Brenda Lougheed, both of Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/057,863

(22) Filed: Apr. 9, 1998

Related U.S. Application Data

(63) Continuation-in-part of application No. 08/835,941, filed on Apr. 11, 1997, now Pat. No. 5,952,203.

(51) Int. Cl.$^7$ ............................. C12P 19/18; C12P 19/04; C12N 11/12; C12N 9/10
(52) U.S. Cl. ........................... 435/97; 435/100; 435/101; 435/174; 435/179; 435/193
(58) Field of Search ............................. 435/89, 91.1, 97, 435/174, 177, 180, 100, 101, 179, 193

(56) References Cited

U.S. PATENT DOCUMENTS

| 4,859,590 | 8/1989 | Thiem et al. | 435/97 |
| 5,374,655 | 12/1994 | Kashem et al. | 514/540 |
| 5,716,812 | 2/1998 | Withers et al. | 435/74 |
| 5,750,389 | 5/1998 | Elling et al. | 435/193 |

FOREIGN PATENT DOCUMENTS

| WO 92/16640 | 10/1992 | (WO) . |
| WO 94/01540 | 1/1994 | (WO) . |
| WO 96/32491 | 10/1996 | (WO) . |
| WO 97/21822 | 6/1997 | (WO) . |

OTHER PUBLICATIONS

Wong, et al., "Enzyme–catalyzed synthesis of N–acetyllactosamine with in situ regeneration of uridine 5'–diphosphate glucose and uridine 5'–diphosphate galactose," *J. Org. Chem.*, 47:5416–5418 (1982).
Paulson et al., *J. Biol. Chem.* 264:17615–17618 (1989).
Saxena et al., *J. Bacteriology* 1419–1424 (1995).
Dabkowski et al., *Transplant Proc.* 25:2921 (1993).
Yamamoto et al., *Nature* 345:229–233 (1990).
Palcic et al., *Carbohydrate Res.* 190:1–11 (1989).
Prieels et al., *J. Biol. Chem.* 256:10456–10463 (1981).
Nunez et al., *Can. J. Chem.* 59:2086–2095 (1981).
Dumas et al., *Bioorg. Med. Letters* 1:425–428 (1991).
Kukowska–Latallo et al., *Genes and Development* 4:1288–1303 (1990).
Mollicone et al., *Eur. J. Biochem.* 191:169–176 (1990).
Stagljar et al., *Proc. Natl. Acad. Sci. USA* 91:5977–5981 (1994).
Heesen et al., *Eur. J. Biochem.* 224:71–79 (1994).
Nagata et al., *J. Biol. Chem.* 267:12082–12089 (1992).
Smith et al., *J. Biol Chem.* 269:15162–15171 (1994).
Homa et al., *J. Biol Chem.* 268:12609–12616 (1993).
Hull et al., *BBRC* 176:608–615 (1991).
Ihara et al., *J. Biolchem.* 113:692–698 (1993).
Shoreiban et al., *J. Biol. Chem.* 268:15381–15385 (1993).
Bierhuizen et al., *Proc. Natl. Acad. Sci. USA* 89:9326–9330(1992).
Rajput et al., *Biochem J*. 285:985–992 (1992).
Hayashi et al., *Chem. Lett.* 1747–1750 (1984).

*Primary Examiner*—David M. Naff
(74) *Attorney, Agent, or Firm*—Townsend and Townsend and Crew LLP

(57) ABSTRACT

Glycosylated acceptors are prepared using glycosyl transferase and activated glycosyl derivatives as donor sugars without the use of sugar nucleotides as donor sugars. A reaction mixture composition containing an activated glycoside derivative such as glycosyl fluoride or glycosyl mesylate, an acceptor substrate such as lactose or other oligosaccharide, a glycosyl transferase and a catalytic amount of a nucleotide phosphate or nucleotide phosphate analog is reacted to produce the glycosylated acceptor. The acceptor substrate may also be a monosaccharide, a fluorescent-labeled saccharide or a saccharide derivative such as an aminoglycoside antibiotic. The glycosyl transferase may be immobilized by removing its membrane-binding domain and attaching in its place a cellulose-binding domain. In another embodiment, a glycosylated acceptor is formed by making a nucleotide phosphate glycoside in situ in a steady state concentration. This process is carried out by admixing in an aqueous medium an activated glycoside derivative, a glycosyl transferase, a member selected from the group consisting of a nucleotide phosphate and a nucleotide phosphate analog, a nucleotide phosphate sugar-dependent enzyme and an acceptor substrate. The glycosyl transferase catalyzes the reaction of the activated glycoside derivative with the nucleotide phosphate or analog to form the nucleotide phosphate glycoside in situ, and the nucleotide phosphate sugar-dependent enzyme catalyzes the reaction of the nucleotide phosphate glycoside with the acceptor substrate to form the glycosylated acceptor.

39 Claims, 15 Drawing Sheets

Inverting Mechanism

+ UDP

Retaining Mechanism

+ UDP

System 1: FCHASE-galactose acceptor
(+)Control, contains lgtC-18 enzyme
Donor substrate: UDP-galactose System 1: FCHASE-galactose acceptor
Test, enzyme is present
Donor substrate: α-galactosyl fluoride

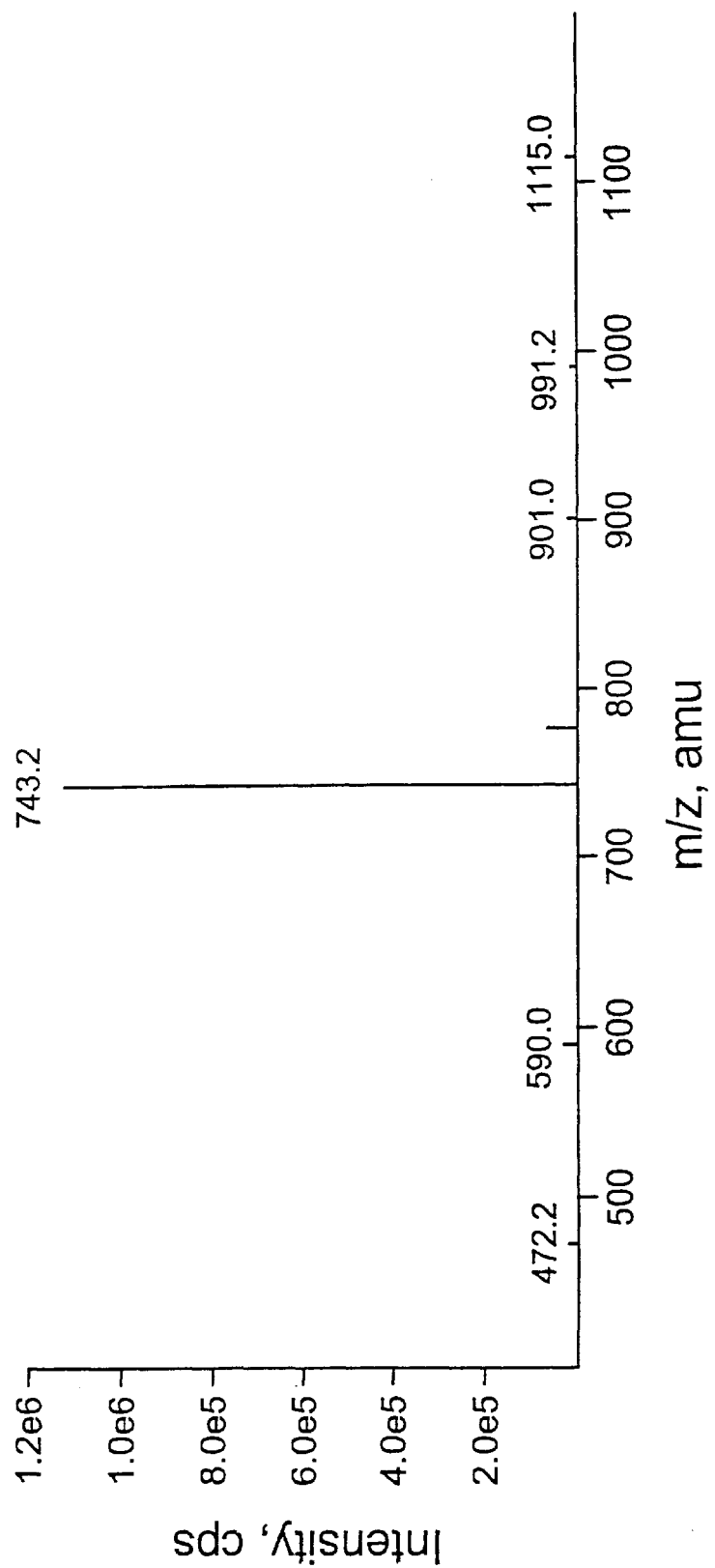

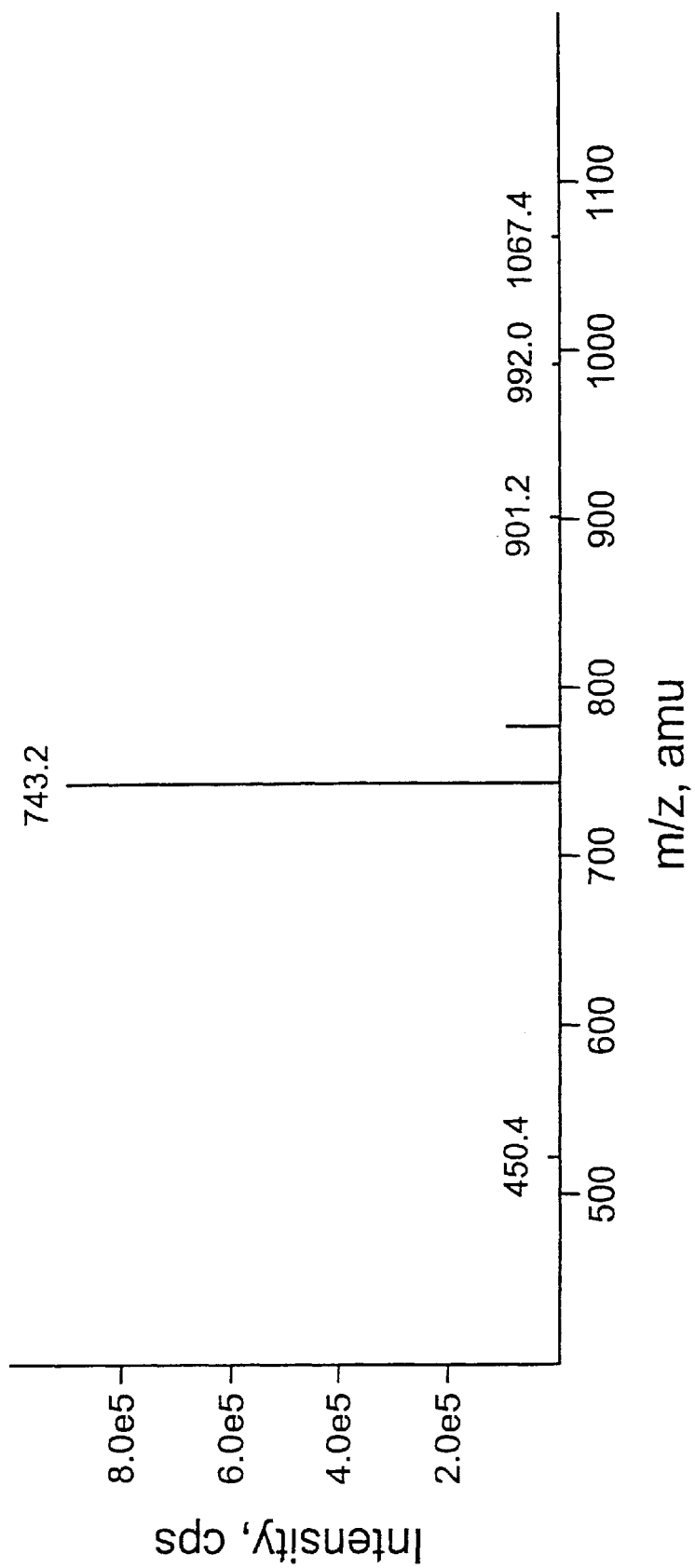

System 1. FCHASE-galactose standard

System 2: FITC-lactose acceptor
(+)Control, contains lgtC-18 enzyme
Donor substrate: UDP-galactose

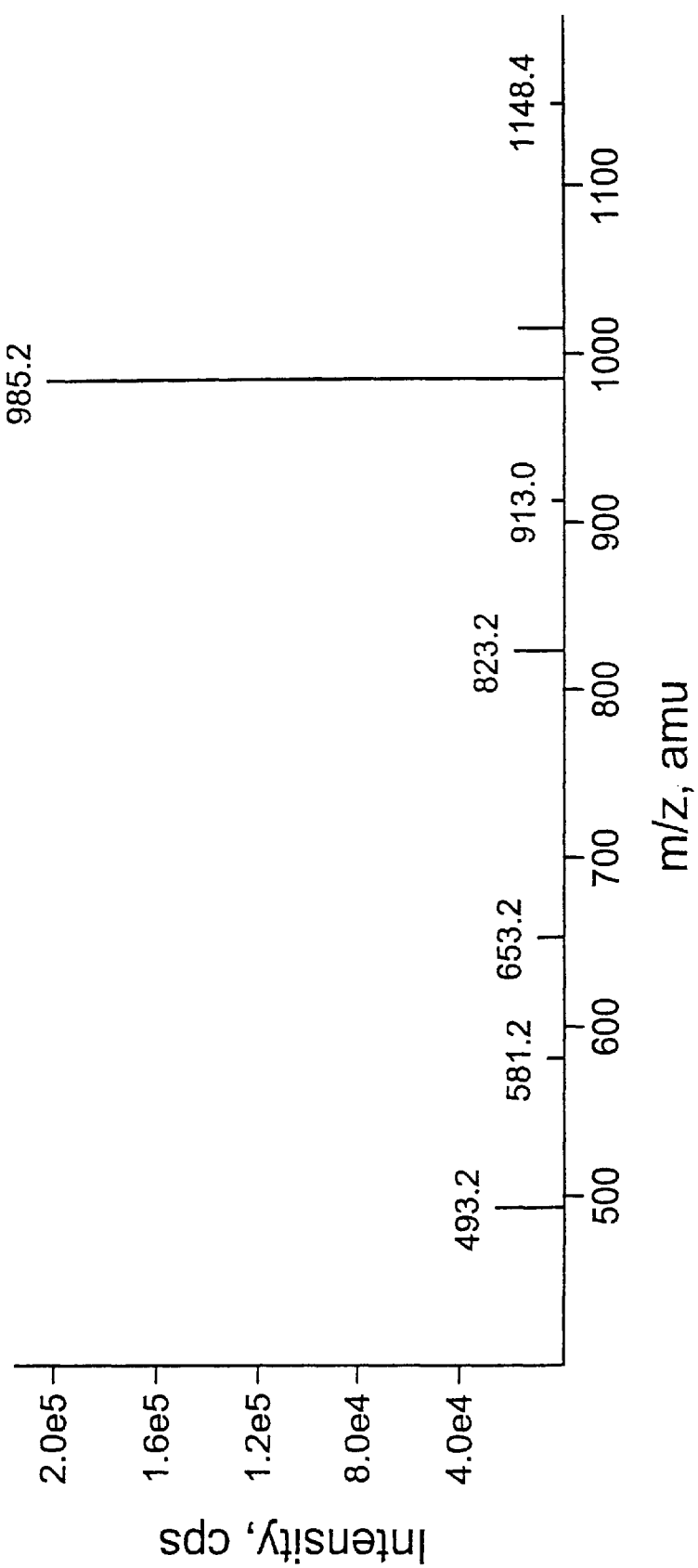

System 2: FITC-lactose acceptor
(-)Control, contains 100 mM buffer, no enzyme
Donor substrate: UDP-galactose System 2: FITC-lactose acceptor
(−)Control, contains 100 mM buffer, no enzyme
Donor substrate: α-galactosyl fluoride

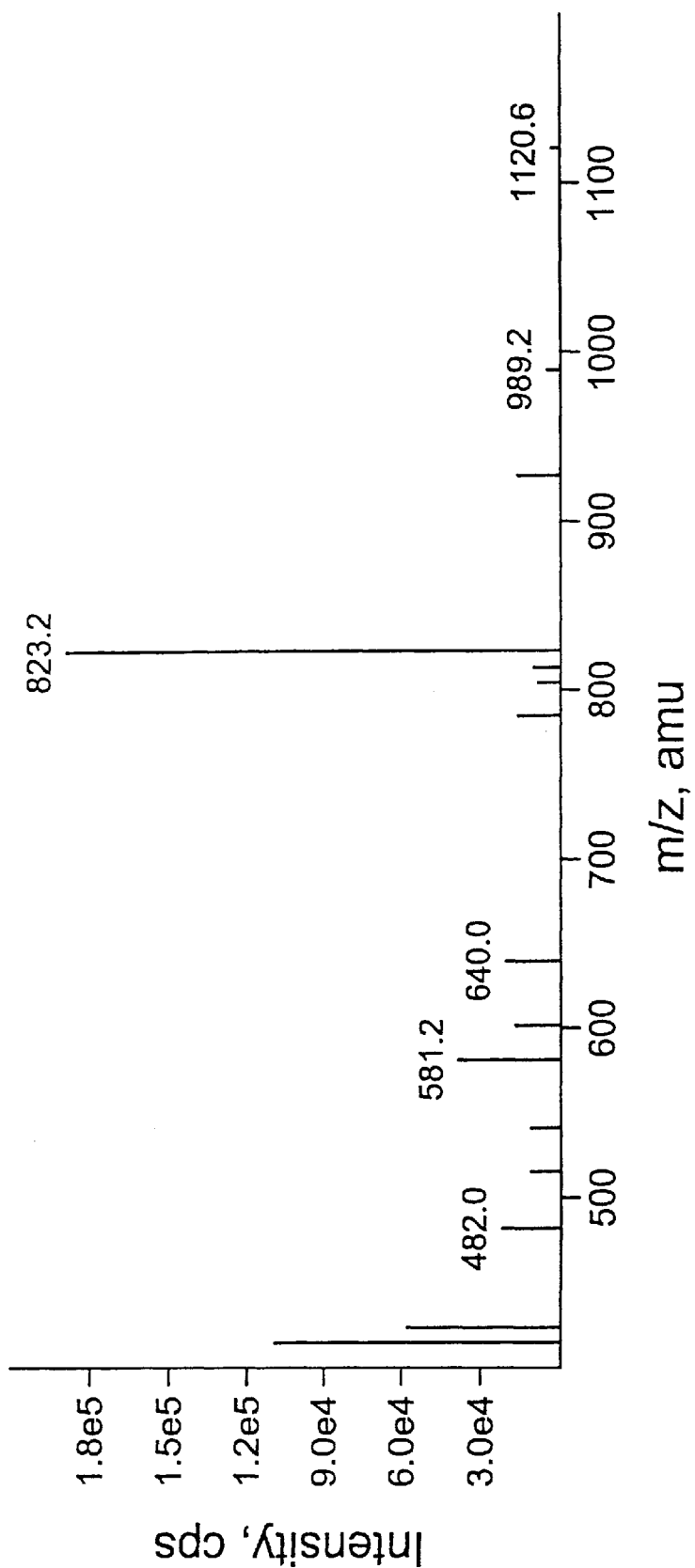
Fig. 4b(E)  System 2. FITC-lactose standard

GLYCOSYLATED ACCEPTOR SYNTHESIS CATALYZED BY GLYCOSYL TRANSFERASE AND NUCLEOTIDE PHOSPHATE SUGAR-DEPENDENT ENZYME

This application is a Continuation-in-Part of U.S. patent application Ser. No. 08/835,941 filed Apr. 11, 1997, now U.S. Pat. No. 5,952,203.

FIELD OF THE INVENTION

In one aspect, this invention relates to the synthesis of oligosaccharides. In particular, it relates to improved syntheses of oligosaccharides using non-naturally occurring glycoside derivatives. In addition, this invention relates to methods of generating nucleotide phosphate sugars in situ and analogs thereof.

BACKGROUND OF THE INVENTION

Oligosaccharides are compounds with considerable potential both as therapeutics and as reagents for clinical assays. Synthesis of many oligosaccharides of potential interest is difficult because of the very nature of the saccharide subunits. A multitude of positional isomers in which different substituent groups on the sugars become involved in bond formation, along with the potential formation of different anomeric forms, are possible. As a result of these problems, large scale chemical synthesis of most oligosaccharides is not possible due to economic considerations arising from the poor yields of desired products.

Enzymatic synthesis provides an alternative to chemical synthesis of oligosaccharides. Enzymatic synthesis using glycosidases, glycosyl transferases, or combinations thereof, have been considered as a possible approach to the synthesis of oligosaccharides.

Glycosidases catalyze the reaction:

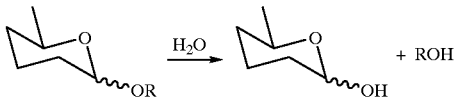

and synthesize oligosaccharides when the natural reaction is run in reverse. Oligosaccharides may also be synthesized by adding a second sugar to the reaction mixture which competes with water, reacting in its place with the first sugar in a transglycosylation reaction. While glycosidases are generally available and easy to handle, difficulties controlling the reverse reaction result in poor yields of product. Additionally, although stereochemical control (i.e., the formation of only one anomer) is good, it is difficult to predict or control the regiochemistry (i.e., the formation of 1–2 versus 1–3 versus 1–4 versus 1–6 bonds).

Glycosyl transferases catalyze the reaction:

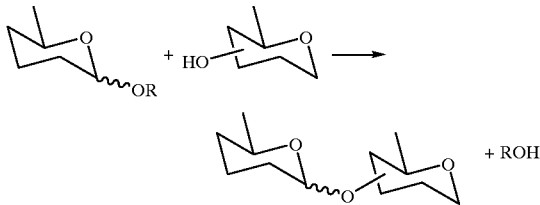

Glycosyl transferases naturally function to synthesize oligosaccharides. They produce specific products with excellent stereochemical and regiochemical control. This reaction proceeds with substantial yield because the reverse reaction does not occur. Unfortunately, because they are often membrane-associated, these enzymes tend to be unstable in solution and expensive to buy. In addition, the sugar nucleotide substrates required by these enzymes are quite expensive. Furthermore, glycosyl transferases possessing the desired specificity to make many interesting oligosaccharides are not commercially available. Recent progress in cloning techniques, however, have made several glycosyl transferases available in sufficient quality and quantity, making enzymatic oligosaccharide synthesis more practical (see, for example, Paulson, et al., *J. Biol. Chem.* 264:17615 (1989)).

To realize the potential of enzymatic oligosaccharide synthesis, there is therefore a need for a synthetic approach which avoids the principal drawbacks of the known techniques (i.e., the cost of the sugar nucleotide substrates). It is an object of this invention to provide such a technique which permits the synthesis of a wide variety of oligosaccharides in good yield.

SUMMARY OF THE INVENTION

The present invention provides methods of preparing oligosaccharides using activated glycoside derivatives. In one aspect, this invention relates to a process for making a glycosylated acceptor, by mixing in an aqueous medium an activated glycoside derivative, an acceptor substrate, a glycosyl transferase, and a nucleotide phosphate or a nucleotide phosphate analog to form a glycosylated acceptor.

In another aspect, this invention relates to a process of making a nucleotide phosphate glycoside, by mixing in an aqueous medium an activated glycoside derivative, a glycosyl transferase and a nucleotide phosphate or a nucleotide phosphate analog, to form a nucleotide phosphate glycoside.

In yet another aspect, this invention relates to a process of making saccharides, oligosaccharides or carbohydrate containing moieties using a nucleotide phosphate glycoside coupled with a nucleotide phosphate sugar dependent enzyme.

The products of the foregoing methods will typically be isolated or recovered following enzymatic synthesis, although in some embodiments, multiple glycosylation reactions will be carried out either in a single reaction vessel or multiple vessels.

In other aspects, the present invention provides compositions which are useful for the formation of glycosidic linkages and compositions which are formed by the methods described herein.

DETAILED DESCRIPTION OF THE INVENTION

Figure 1:
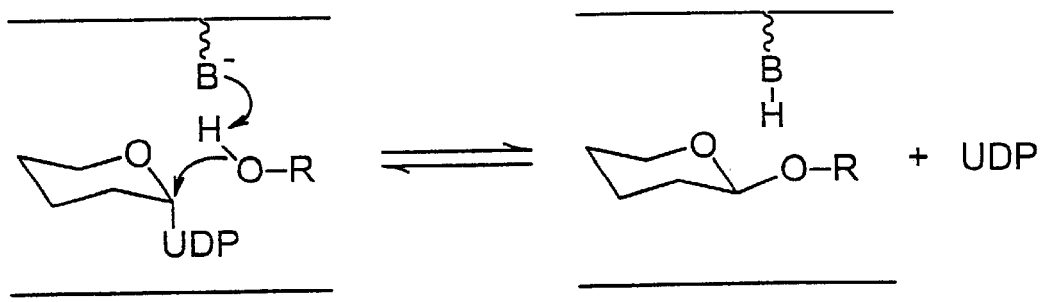
FIGS. 1 and 2 show proposed inverting and retaining mechanisms for glycosyl transfer with β-glycosyl transferases and α-glycosyl transferases (see, Saxena, et al., *J. Bacteriology*, 1419 (1995)).
Figure 2:
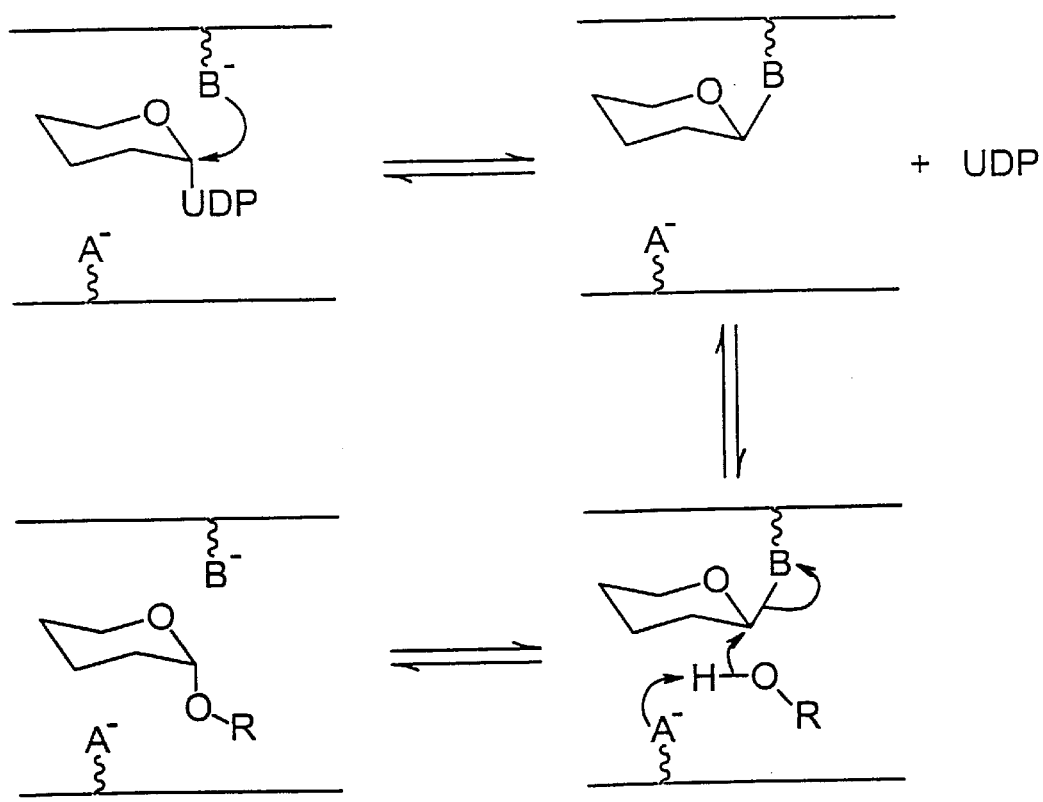
Figure 3:
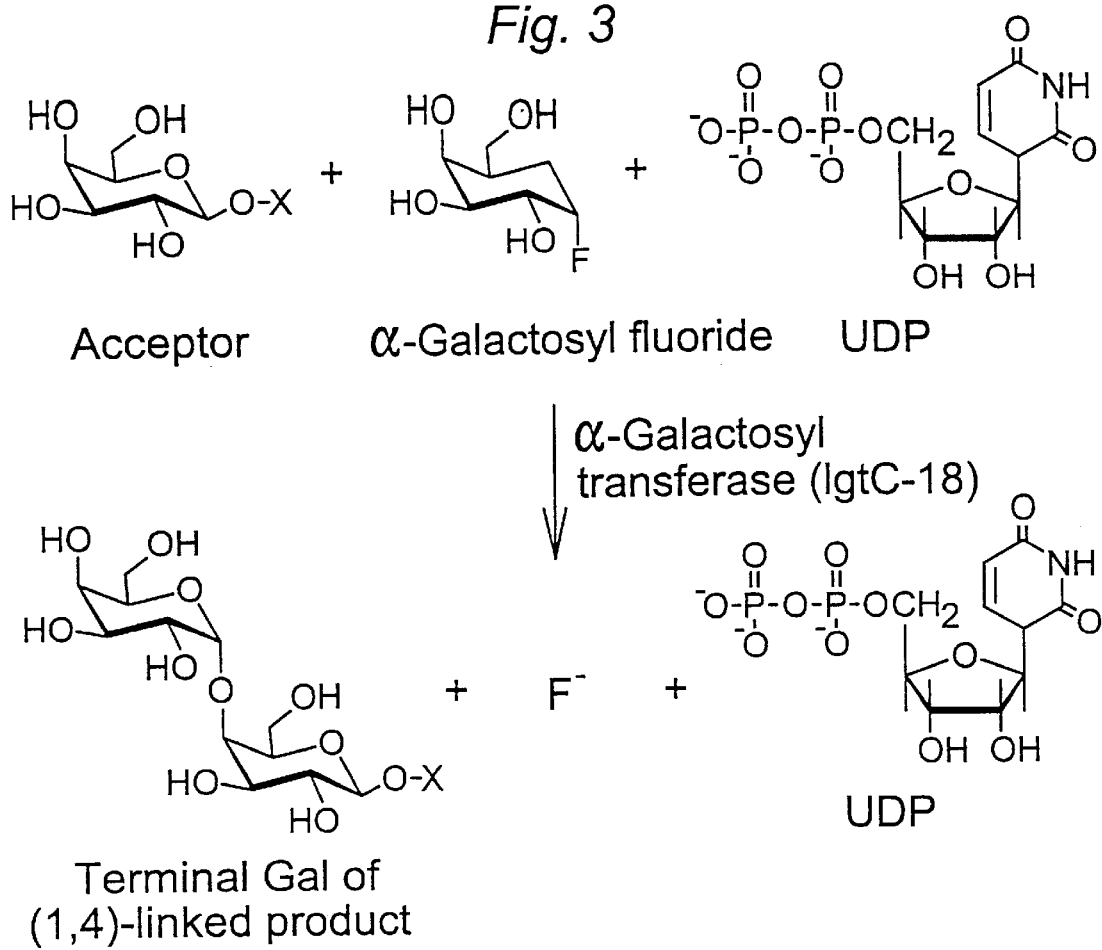
FIG. 3 shows the α-galactosyl transferase (lgtC-18) mediated coupling of α-galactosyl fluoride and either FCHASE-galactose or FITC-lactose which occurs in the presence of UDP.
Figure 3:
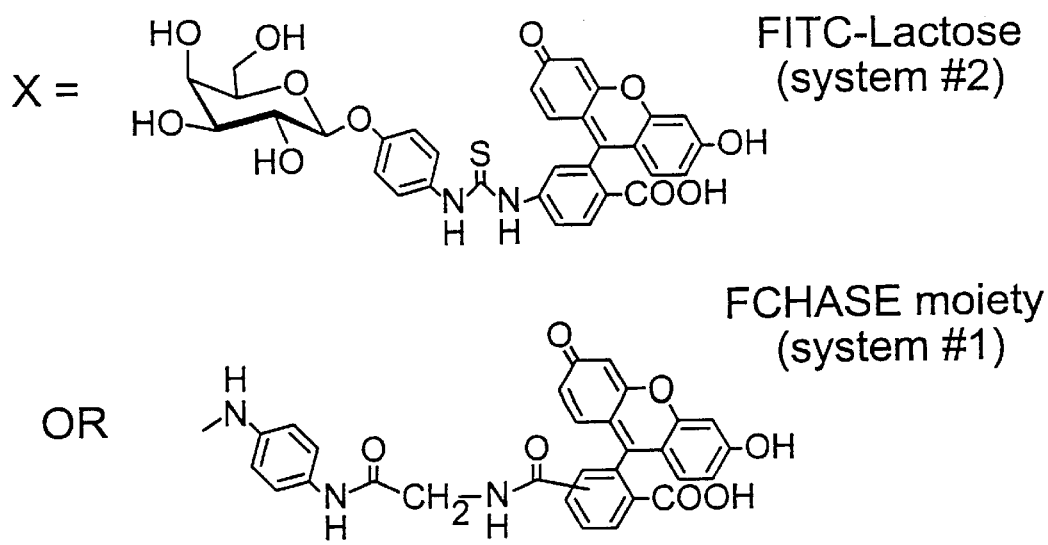
Figure 4A:
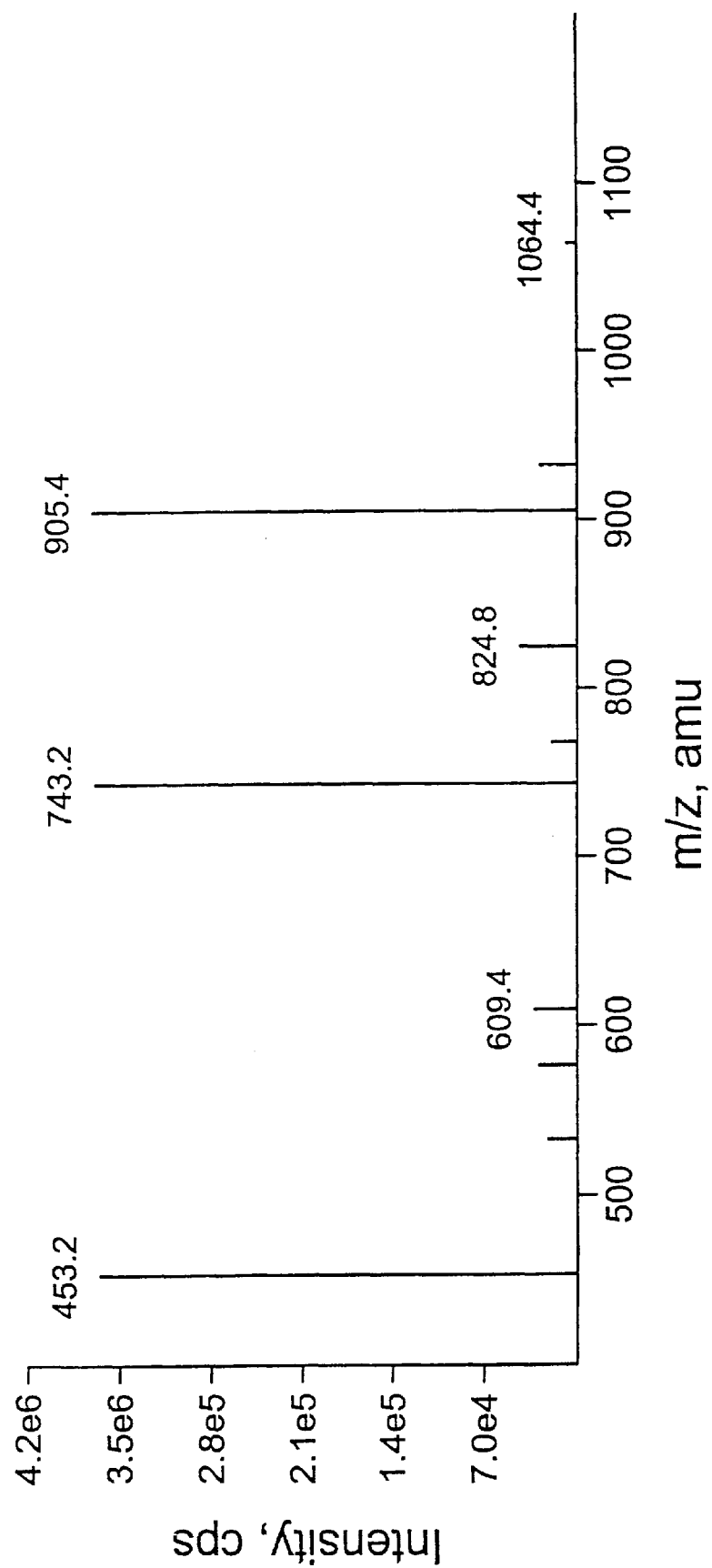
FIGS. 4a(A–E) and 4b(A–E) show the mass spectra of the reaction products obtained using either FCHASE-galactose or FITC-lactose as acceptors for the enzyme mediated reaction of FIG. 3.
Figure 4A:
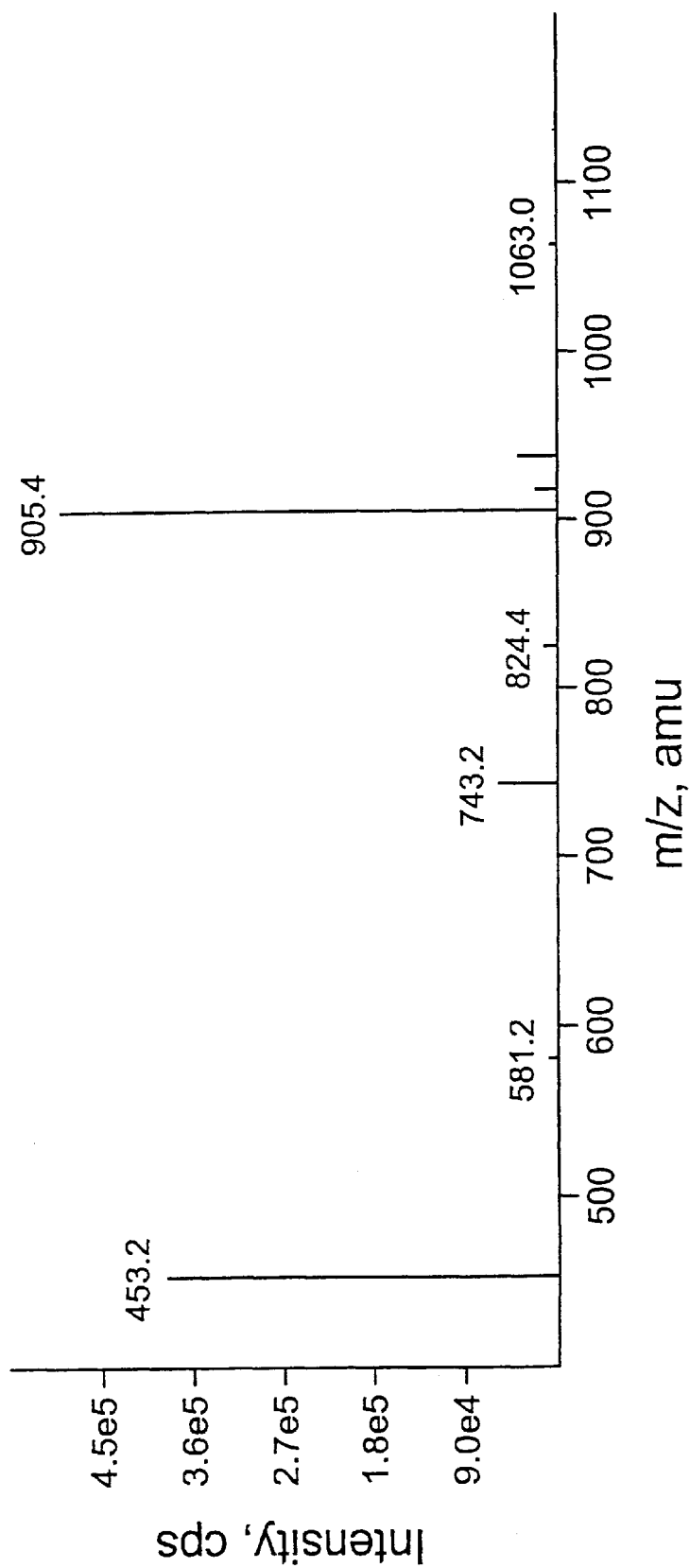
Figure 4A:
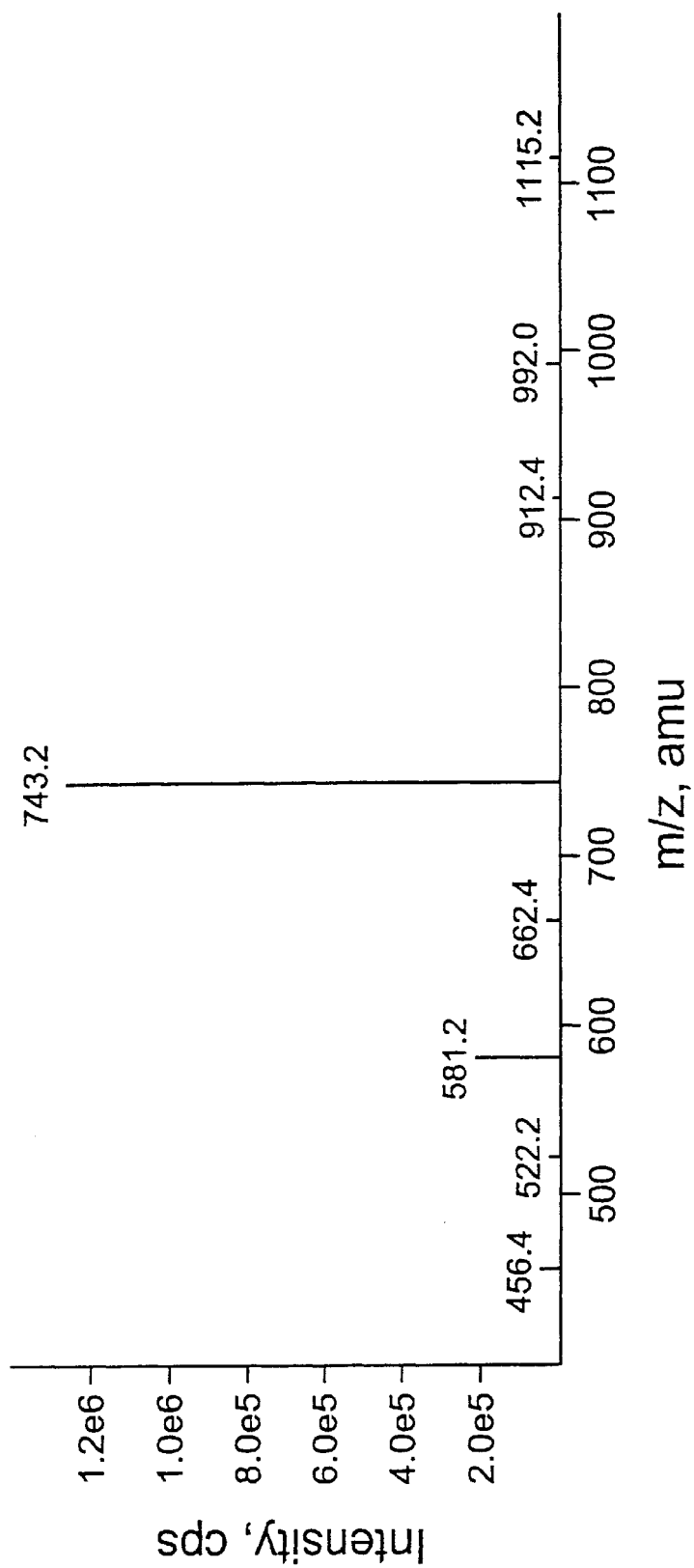
Figure 4B:
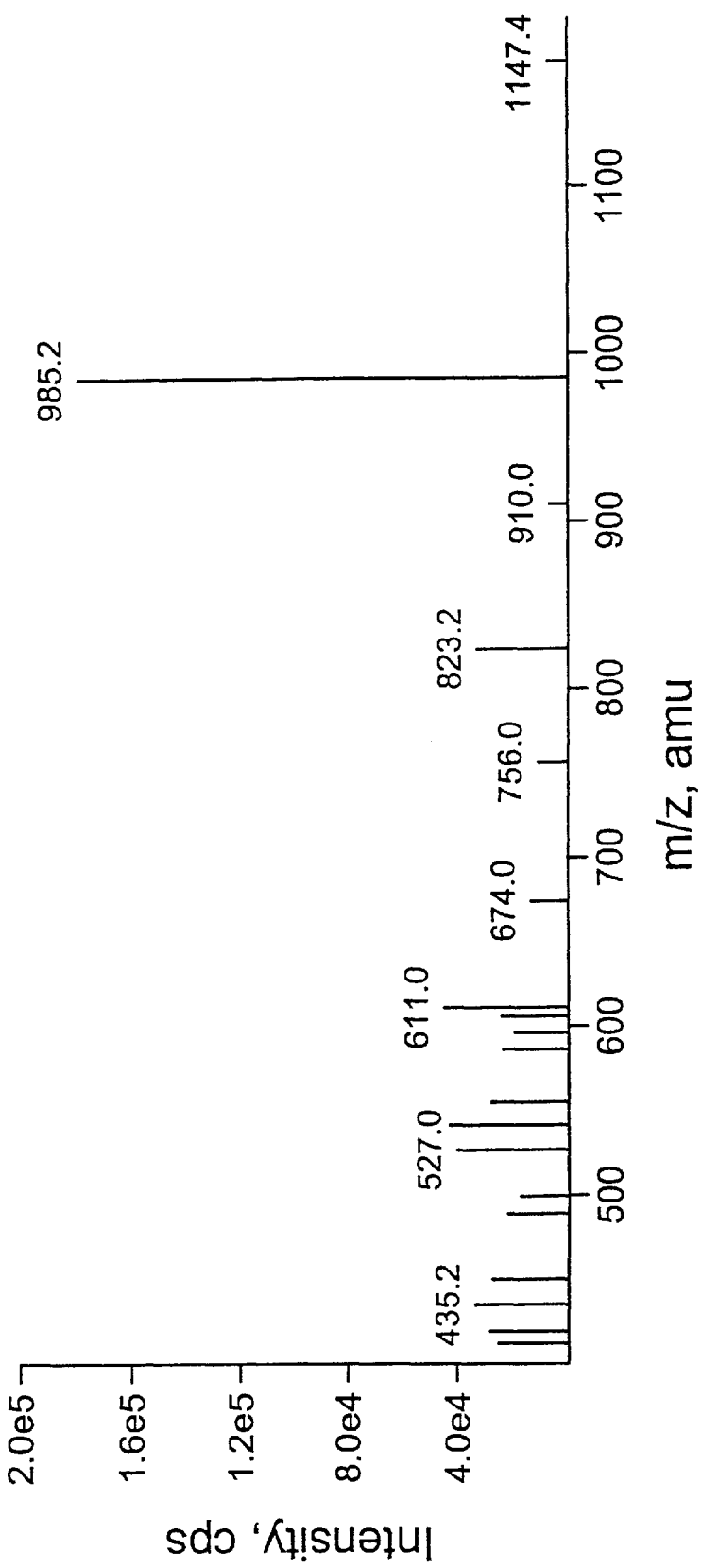
Figure 4B:
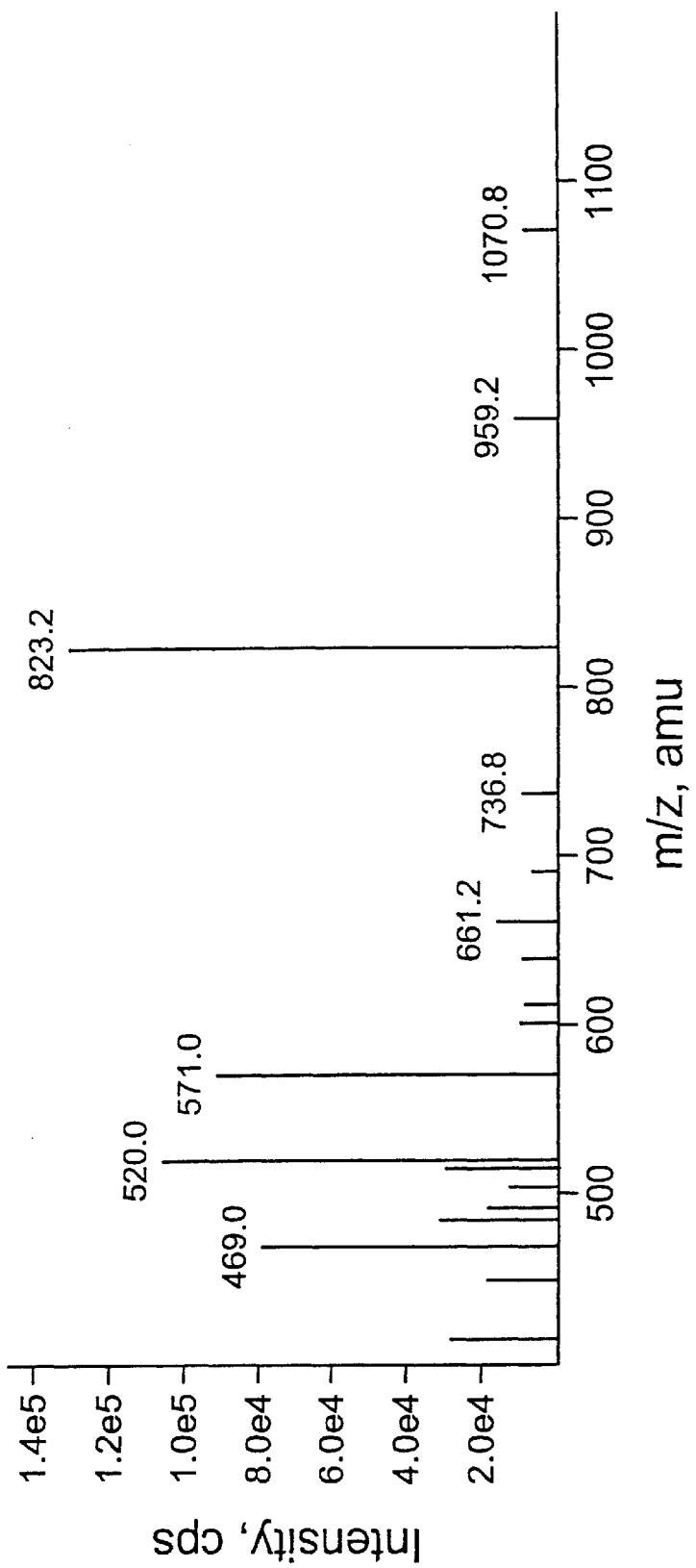
Figure 4B:
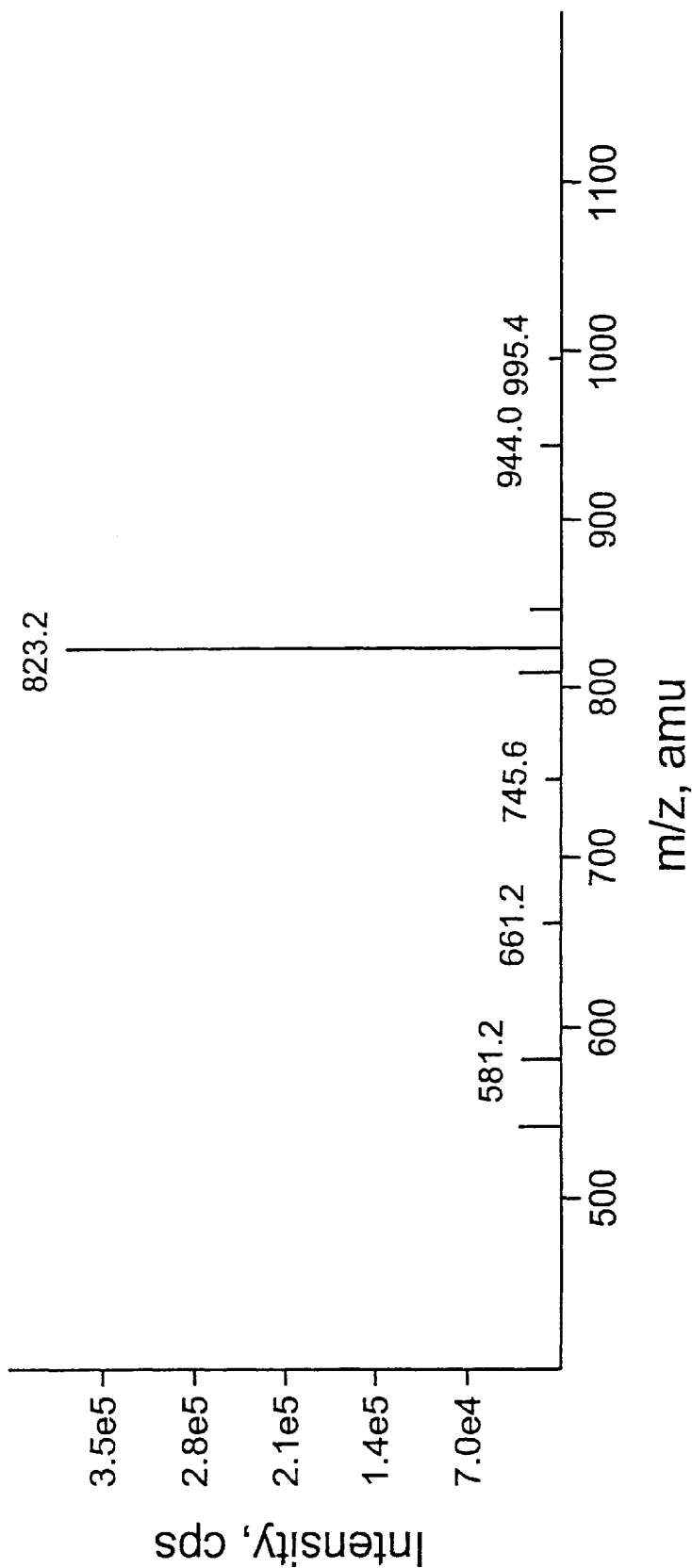

The present invention provides methods of forming oligosaccharides using activated glycosyl derivatives as donor sugars in the enzymatic synthesis of oligosaccharides by glycosyl transferases. These donor sugars act as alternates to the naturally-occurring substrates. Normally, these enzymes utilize nucleotide diphosphosugars or nucleotide monophosphosugars in which the nucleotide phosphate is $\alpha$-linked to the 1-position of the sugar. The product formed is either a $\beta$-linked or an $\alpha$-linked glycosyl glycoside following transfer to an appropriate acceptor saccharide.

The transferases forming $\beta$-linked products are called $\beta$-glycosyl transferases and are believed to act via an inverting mechanism, whereas those which form $\alpha$-linked products are $\alpha$-glycosyl transferases and are thought to operate via a mechanism involving retention of configuration at the reactive center. The actual mechanism of these reactions is speculative and is based primarily on studies performed using glycosidases. Abundant sources of glycosyl transferases have only recently been developed using recombinant techniques. Consequently, comprehensive study of this class is in its infancy. To date, there are still no published x-ray crystal structures for any nucleotide phosphosugar-dependent glycosyl transferases.

The methods of the present invention can be used to make a wide variety of oligosaccharides. Particularly useful oligosaccharides which can be made by this method include mimics of antigens found on cell surfaces. These cell surface oligosaccharides are important for cell-cell recognition and have been implicated as receptor sites for bacterial toxins such as those of the Shiga-toxin family which bind to antigens having the structure $\alpha$-gal-(1,4)-$\beta$-gal-(1,4)-$\beta$-glc-lipopolysaccharide. These toxins, for example, *E. coli* O157, are implicated in hemorrhagic colitis and hemolytic-uremic syndrome. The use of a synthetic oligosaccharide to bind/neutralize these toxins has been tested and appears to work in animal studies. However, the $\alpha$-gal linkage has proven difficult to prepare using conventional synthetic methods. Using the methods provided herein, formation of this linkage can be carried out in a single step to provide pure products.

As used herein, the sugars have their standard abbreviations, including:

Ara=arabinosyl; Fru=fructosyl; Fuc=fucosyl; Gal=galactosyl; GalNAc=N-acetylgalacto; Glc=glucosyl; GlcNAc=N-acetylgluco; IdA=iduronic acid; Man=mannosyl; and NeuAc=sialyl (N-acetylneuraminyl).

Embodiments of the Invention

In one aspect, this invention relates to a process for making a glycosylated acceptor, by mixing in an aqueous medium an activated glycoside derivative, an acceptor substrate, a glycosyl transferase, and a catalytic amount of a nucleotide phosphate or a nucleotide phosphate analog to form a glycosylated acceptor.

In a preferred embodiment, this invention relates to a process for making a glycosylated acceptor comprising:

(a) admixing in an aqueous medium an activated glycoside derivative, a glycosyl transferase, an acceptor substrate, and a catalytic amount of a nucleotide phosphate or a nucleotide phosphate analog, to form an aqueous reaction mixture; and (b) maintaining the aqueous reaction mixture at a pH value of about 5 to about 10, and at a temperature of about 0° C. to about 40° C., for a period of time sufficient for glycosylation of the acceptor substrate to occur, and form a glycosylated acceptor.

In certain preferred embodiments, this aspect of the invention will further comprise the step of:

(c) recovering the glycosylated acceptor.

Activated glycoside derivatives which are useful in the present invention are typically glycosides which have been synthetically altered to include an activated leaving group. As used herein, the term "activated leaving group" refers to those moieties which are easily displaced in enzyme-regulated nucleophilic substitution reactions. Examples of such groups include, for example, fluoro, chloro, bromo, tosylate ester, mesylate ester, triflate ester and the like. One constraint on the activated leaving group, for use in the present invention, is that it should not sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, $\alpha$-galactosyl fluoride, $\alpha$-mannosyl fluoride, $\alpha$-glucosyl fluoride, $\alpha$-fucosyl fluoride, $\alpha$-xylosyl fluoride, $\alpha$-sialyl fluoride, $\alpha$-N-acetylglucosaminyl fluoride, $\alpha$-N-acetylgalactosaminyl fluoride, $\beta$-galactosyl fluoride, $\beta$-mannosyl fluoride, $\beta$-glucosyl fluoride, $\beta$-fucosyl fluoride, $\beta$-xylosyl fluoride, $\beta$-sialyl fluoride, $\beta$-N-acetylglucosaminyl fluoride and $\beta$-N-acetylgalactosaminyl fluoride are most preferred.

Glycosyl fluorides can be prepared from the free sugar by first acetylating the sugar and then treating it with HF/pyridine. This will generate the thermodynamically most stable anomer of the protected (acetylated) glycosyl fluoride (i.e., the $\alpha$-glycosyl fluoride). If the less stable anomer (i.e., the $\beta$-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

The acceptor substrates used in the present methods can be essentially any monosaccharide or oligosaccharide having a terminal saccharide residue for which the particular glycosyl transferase exhibits specificity. The acceptor substrate may be substituted at the position of its non-reducing end. Thus, the glycoside acceptor may be a monosaccharide, an oligosaccharide, a fluorescent-labeled saccharide, or a saccharide derivative such as an aminoglycoside antibiotic. In one group of preferred embodiments, the glycoside acceptor is a saccharide derivative, preferably an aminoglycoside. In another group of preferred embodiments, the glycoside derivative is an oligosaccharide, preferably lactose, Gal$\beta$ (1–3)GlcNAc, Galβ(1–4)GlcNAc, Galβ(1–3)GalNAc, Galβ(1–4)GalNAc, sialyl lactose, Galβ(1–3)GalNAcβ(1–4), GalNAcβ(1–4)-lactose, Gangliosides GM1, GM2, GM3, GD3, GlcNAcβ(1–3)-lactose; GlcNAcβ(1–3)galactose; Galβ(1–4)GlcNAcβ(1–3)galactose; Galβ(1–4)GlcNAc-β(1–3)-lactose; L-IdAβ(1–4)glucosamine; Glucosamineα(1–4)IdA; Galα(1–4)lactose; GlcNAcβ(1–3)Galα(1–4)-lactose; Galβ(1–3)GalNAcβ(1–3)Galα(1–4)lactose; GalNAcβ(1–3)Galα(1–4)lactose; GlcNAcβ(1–3)Gal; Galβ(1–3)GlcNAcβ(1–3)Gal; Fucα(1–2)Galβ(1–3)GlcNAcβ(1–3)Gal; Fucα(1–4)GlcNaβ(1–3)Gal; Fucα(1–4)-GlcNAc-β(1–3)Gal; Galβ(1–3); Fucα(1–3)GlcNAc; Fucα(1–3)-GlcNAc Galβ(1–4) Galβ(1–3)GlcNAcβ(1–3)Gal; and ceramide glycosides of the above. In still other preferred embodiments, the glycoside acceptor is a labeled saccharide, more preferably a fluorescent-labeled saccharide, most preferably F-ITC-lactose, FCHASE-lactose, FITC-galactose, FCHASE-galactose, p-nitrophenyl glucoside and p-nitrophenyl maltohexoside.

A number of commercially and/or therapeutically important oligosaccharides and derivatives can be prepared using the methods described herein. Accordingly, examples of acceptor substrates which could be glycosylated to provide therapeutically useful oligosaccharides and derivatives include, for example, lactose and other members of the list provided above.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2–3, 2→3, (2–3) or (2,3). Each saccharide is a pyranose.

An additional component present in the reaction mixtures is a nucleotide phosphate (including nucleotide mono-, di- or triphosphates) or analog thereof. Importantly, it has been found that the methods herein can be conducted in the presence of catalytic amounts of a nucleotide phosphate or analog thereof. Nucleotide monophosphates which are suitable for use in the present invention include, but are not limited to, adenosine monophosphate (AMP), cytidine monophosphate (CMP), uridine monophosphate (UMP), guanosine monophosphate (GMP), inosine monophosphate (IMP) and thymidine monophosphate (TMP). Nucleotide triphosphates suitable for use in accordance with the present invention include adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleotide triphosphate is UTP. Preferably, the nucleotide phosphate is a nucleotide diphosphate, for example, adenosine diphosphate (ADP), cytidine diphosphate (CDP), uridine diphosphate (UDP), guanosine diphosphate (GDP), inosine diphosphate (IDP) and thymidine diphosphate (TDP). A preferred nucleotide diphosphate is UDP. As noted above, the present invention can also be practiced with an analog of the nucleotide phosphates. Suitable analogs include, but are not limited to, nucleotide sulfates and sulfonates. Still other analogs include simple phosphates, for example, pyrophosphate.

Glycosyl transferases which are useful in the present invention include, for example, α-sialyl transferases, α-glucosyl transferases, α-galactosyl transferases, α-fucosyl transferases, α-mannosyl transferases, α-xylosyl transferases, α-N-acetyl hexosaminyl transferases, β-sialyl transferases, β-glucosyl transferases, β-galactosyl transferases, β-fucosyl transferases, β-mannosyl transferases, β-xylosyl transferases, and β-N-acetyl hexosaminyl transferases such as those from *Neisseria meningitidis*, or other bacterial sources, and those from rat, mouse, rabbit, cow, pig, and human sources. Preferably the glycosyl transferase is a mutant glycosyl transferase enzyme in which the membrane-binding domain has been deleted.

Exemplary galactosyltransferases include oa(1,3) galactosyltransferase (E.C. No. 2.4.1.151, see, e.g., Dabkowski, et al., *Transplant Proc.* 25:2921 (1993) and Yamamoto, et al. *Nature* 345:229–233 (1990)) and α(1,4) galactosyltransferase (E.C. No. 2.4.1.38). A number of fucosyltransferases are known to those of skill in the art. Suitable fucosyltransferases then include the known βGal(1→3,4)βGlcNAc α(1→3,4)fucosyltransferase (FTIII E.C. No. 2.4.1.65) which is obtained from human milk (see, Palcic, et al., *Carbohydrate Res.* 190:1–11 (1989); Prieels, et al., *J. Biol. Chem.* 256:10456–10463 (1981); and Nunez, et al., *Can. J. Chem.* 59:2086–2095 (1981)) and the βGal(1→4)βGlcNAc α(1→3)fucosyltransferases (FTIV, FTV, FTVI, and FTVII, E.C. No. 2.4.1.65) which are found in human serum. A recombinant form of βGal(1→3,4)βGlcNAc α(1→3,4) fucosyltransferase is also available (see, Dumas, et al., *Bioorg. Med. Letters* 1:425–428 (1991) and Kukowska-Latallo, et al., *Genes and Development* 4:1288–1303 (1990)). Other exemplary fucosyltransferases include α1,2 fucosyltransferase (E.C. No. 2.4.1.69). Enzymatic fucosylation may be carried out by the methods described in Mollicone, et al., *Eur. J. Biochem.* 191:169–176 (1990) or U.S. Pat. No. 5,374,655.

One of skill in the art will understand that other glycosyltransferases can be substituted into the present methods such as a sialyltransferase. Still other glucosyltransferases include a glycosyltransferase which can also be, e.g., Alg8 (Stagljov, et al., *Proc. Natl. Acad. Sci. USA* 91:5977 (1994)) or Alg5 (Heesen, et al. *Eur. J. Biochem.* 224:71 (1994)). Suitable N-acetylgalactosaminyltransferases include α(1,3) N-acetylgalactosaminyltransferase, β(1,4) N-acetylgalactosaminyltransferases (Nagata, et al. *J. Biol. Chem.* 267:12082–12089 (1992) and Smith, et al. *J. Biol Chem.* 269:15162 (1994)) and polypeptide N-acetylgalactosaminyltransferase (Homa, et al. *J. Biol Chem.* 268:12609 (1993)). Suitable N-acetylglucosaminyltransferases include GnTI (2.4.1.101, Hull, et al., BBRC 176:608 (1991)), GnTII, and GnTIII (Ihara, et al. *J. Biolchem.* 113:692 (1993)), GnTV (Shoreiban, et al. *J. Biol. Chem.* 268: 15381 (1993)), O-linked N-acetylglucosaminyltransferase (Bierhuizen, et al. *Proc. Natl. Acad. Sci. USA* 89:9326 (1992)), N-acetylglucosamine-1-phosphate transferase (Rajput, et al. *Biochem J.*285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

It will be readily apparent to those skilled in the art that glycosyl transferases can be mutated or altered to achieve improved properties. These alterations include, but are not limited to, site specific mutagenesis, directed evolution, deletion of the membrane-binding domain, and the like. Thus, the present invention includes all such mutations, alterations and modifications.

In addition, the present invention includes glycosyl transferases that in their native state are unable to utilize an activated glycoside derivative as a substrate, however by some mutation, or directed evolution the enzyme can use an activated glycoside as a substrate.

The generation and testing of several mutants of a glycosyltransferase is generally described in Wakarchuk, W. W., Cunningham, A.-M., Watson, D. C. and Young, N. M., "Role of Paired Basic Residues in the Expression of Active Recombinant Galactosyltransferases from the Bacterial Pathogen *Neisseria meningitidis*" (1998) Protein Engineering, In Press.

In other embodiments, the present invention includes conservative substitutions to the glycosyl transferases listed. A conservative substitution, when describing a protein refers to a change in the amino acid composition of the protein that does not substantially alter the protein's activity. Thus, conservatively modified variations of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. (See Creighton (1984) *Proteins*, W. H. Freeman and Company) In addition, individual substitutions, deletions or additions which alter, add or delete a single amino acid or a small percentage of amino acids in an encoded sequence are also conservatively modified variations.

In another embodiment, this invention relates to a process of making a nucleotide phosphate glycoside, by mixing in an aqueous medium an activated glycoside derivative, such as those described herein, with a glycosyl transferase and a nucleotide phosphate or a nucleotide phosphate analog, to form a nucleotide phosphate glycoside. The glycosyl transferase will couple the activated glycoside derivative and the nucleotide phosphate or nucleotide phosphate analog to form a nucleotide phosphate glycoside. In a particularly preferred embodiment, this method is used to form a nucleotide phosphate sugar in situ, to be used with a nucleotide phosphate sugar-dependent enzyme. The nucleotide phosphate (including nucleotide mono-, di- or triphosphates) or analog thereof have been previously defined. In especially preferred embodiments, the nucleotide phosphate sugars generated in situ include the UDP-hexoses such as UDP-galactose, and UDP-glucose.

In another embodiment, the nucleotide phosphate sugar generated in situ, is produced in a steady state concentration which will then be used by a nucleotide phosphate sugar-dependent enzyme (in another enzymatic reaction). Suitable nucleotide phosphate sugar-dependent enzymes include, but are not limited to, a second glycosyl transferase, an epimerase, a dehydrogenase, a pyrophosphorylase and a nucleotide diphosphate ribosyl transferase.

The nucleotide phosphate sugar-dependent enzymes can be used in enzymatic catalyzed reactions for a variety of acceptor substrates. These acceptor substrates include, but are not limited to, nicotinamide adenine dinucleotide, nicotinamide adenine dinucleotidephosphate, glucose, a glucoside, galactose, a galactoside, mannose, a mannoside, fucose, a fucoside, N-acetylneuraminic acid, an N-acetylneuraminide, xylose, a xyloside, N-acetylglucosamine, an N-acetylglucosaminide, N-acetylgalacotosamine, an N-acetylgalactosaminide, arabinose, an arabinoside, an antibiotic aglycone, a detergent aglycone, a lipid, a sapogenin, an oligosaccharide, a monosaccharide, a fluorescent-labeled saccharide and a saccharide derivative.

In a particular preferred embodiment, "synthesis" enzymes which are unable to use an activated glycosyl derivative directly, can use a nucleotide phosphate sugar or an analog thereof which has been generated in situ by a "coupling enzyme." In this manner, the reaction medium contains a nucleotide phosphate sugar, such as UDP-galactose, which has been generated by a coupling enzyme in situ. In the same reaction medium, a "synthesis enzyme," which uses the nucleotide phosphate sugar, such as UDP-galactose, catalyzes a subsequent reaction with at least one acceptor substrate. The synthesis enzyme could be for example, a nucleotide phosphate sugar dependent enzyme, such as an epimerase. The epimerase is catalyzing the epimerization of the acceptor substrate while utilizing the nucleotide phosphate sugar being supplied by the coupling enzyme. In this way, the coupling enzyme and synthesis enzyme work in tandem. The coupling enzyme supplies a needed nucleotide phosphate sugar to the synthesis enzyme which then can catalyze a reaction on the acceptor substrate. In other embodiments, more than one coupling enzyme and more than one synthesis enzyme are present in the reaction medium.

For those embodiments in which the method is to be practiced on a commercial scale, it can be advantageous to immobilize the glycosyl transferase or other enzymes on a support. This immobilization facilitates the removal of the enzyme from the batch of product and subsequent reuse of the enzyme. Immobilization of glycosyl transferases, for example, can be accomplished, by removing from the transferase its membrane-binding domain, and attaching in its place a cellulose-binding domain. One of skill in the art will understand that other methods of immobilization could also be used and are described in the available literature.

For the above glycosyltransferase reaction mixtures, the concentrations or amounts of the various reactants used in the processes depend upon numerous factors including reaction conditions such as temperature and pH value, and the choice and amount of acceptor substrates to be glycosylated. In general, the upper limit for the concentrations of reactants that can be used in accordance with the method of the present invention is determined by the solubility of such reactants.

Preferably, the concentrations of the activated glycoside derivative, the acceptor substrate, the glycosyl transferase and the nucleotide phosphate or analog thereof are selected such that glycosylation proceeds until the more expensive reagent (acceptor substrate or activated glycoside derivative) is consumed.

The amount of glycosyl transferase which is present in the reaction medium is typically a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The above ingredients are combined by admixture in an aqueous reaction medium (solution). That medium has a pH value of about 5 to about 10. The medium is devoid of chelators that bind enzyme cofactors such as $Mg^{+2}$ or $Mn^{+2}$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8.5, preferably about 7.2 to 7.8, by the addition of base. A suitable base is NaOH, preferably 6 M NaOH.

The reaction medium may also comprise solubilizing detergents (e.g., Triton® or SDS) and organic solvents such as methanol or ethanol, if necessary. In addition, the enzymes are preferably utilized free in solution but can be bound to a support such as a polymer (e.g., cellulose).

The temperature at which an above process is carried out can range from just above freezing to the temperature at which the most sensitive enzyme denatures. That temperature range is preferably about 0° C. to about 40° C., and more preferably at about 20° C. to about 30° C.

The reaction mixture so formed is maintained for a period of time sufficient for the acceptor substrate to be glycosylated to form a desired product. Some of that product can often be detected after a few hours, with recoverable amounts usually being obtained within 24 hours. It is preferred to optimize the yield of the process, and the maintenance time is usually about 36 to about 240 hours.

The products produced by the above processes can be used without purification. However, it is usually preferred to recover the product. Standard, well known techniques are used for recovery of glycosylated saccharides such as thin or thick layer chromatography or ion exchange chromatography. Additionally, one or more column chromatographic techniques can be used for the product recovery. Using such techniques, the saccharides prepared by the above methods of the invention can be produced at essentially 100% purity by proton NMR and TLC.

In one group of embodiments, the activated glycoside derivative and the acceptor substrate are combined in an aqueous buffer (for example 100 mM HEPES buffer, pH 7.5) in a mole ratio (acceptor/donor) of about 1 to 5 together with a catalytic amount of UDP (i.e. about 1 mM) and glycosyl transferase (i.e. about 1.5 mg/mL) and incubated at about 25° C. for a period of time sufficient to produce significant yields of product, for example 1 hr to 3 days depending on the scale of the reaction. To remove the buffer from the product when HEPES buffer is used, the reaction mixture is combined with 25 volumes of deionized water, loaded onto a Sep-Pack™ [18]C cartridge (preconditioned with acetonitrile then water), and rinsed with water. The product is eluted with 50% acetonitrile and concentrated in vacuo. The concentrated solution is then characterized by TLC and mass spectroscopy.

In another aspect, the present invention provides compositions which are useful for the formation of glycosidic linkages. The compositions typically contain in admixture an activated glycoside derivative, a glycosyl transferase, an acceptor substrate, and a catalytic amount of a nucleotide phosphate or a nucleotide phosphate analog. These components, including the preferred embodiments, are essentially those which have been described above.

In yet another aspect, the present invention provides compositions which are prepared by the above processes.

The following examples are offered solely for the purposes of illustration, and are intended neither to limit nor to define the invention.

EXAMPLES

Materials and Methods

Thin-layer chromatography (tlc) separations were performed using Merck Kieselgel 60 $F_{254}$ analytical plates. Compounds were detected visually by charring with 5% sulfuric acid in methanol. Column chromatography was performed using a silica gel column of Kieselgel 60 (230–400 mesh). Solvents were either reagent grade, certified, or spectral grade. Dry methanol was distilled from magnesium methoxide prepared in situ by reaction of methanol with magnesium turnings in the presence of iodine. $^{19}F$ and $^{1}H$-nuclear magnetic resonance (nmr) spectra were recorded on a 200 MHz Bruker AC-200. Chemical shifts are listed in the delta (δ) scale. Compounds run in $CDCl_3$ are referenced against internal deuterium signals. HF-pyridine was purchased from Aldrich. All other chemicals were from Sigma and were used without further purification. Mass spectroscopy was performed using a Perkin-Elmer triple quadrupole LC/MS/MS electrospray mass spectrometer.

Example 1

This example illustrates the synthesis of α-D-galactosyl fluoride.

1.1 Preparation of 1,2,3,4,6-penta-O-acetyl α-D-galactopyranose

Galactose (60 g) was dissolved in dry pyridine (420 mL) then cooled to 0° C. Acetic anhydride (285 mL) was added slowly with stirring and the mixture was allowed to stir for 5 days at room temperature. The reaction was quenched by the addition of ice water (1.5 L). The product was extracted into ethyl acetate (500 mL) and the organic extract was washed with 10% HCl until pH<6, washed with 5% sodium bicarbonate solution until basic to litmus, then with saturated NaCl. Solvent was removed in vacuo to give a white solid in 88% yield (114 g). The product was recrystallized from 95% ethanol (mp 109–110° C., lit. mp 112–113° C.).

1.2 Preparation of 2,3,4,6-tetra-O-acetyl α-D-galactosyl fluoide

The title compound was prepared by the method of Hayashi, et al., *Chem. Lett.* 1747 (1984). Briefly, 1,2,3,4,6-penta-acetyl α-D-galactopyranose (5 g) was dissolved in 70% hydrogen fluoride-pyridine (4 mL/mg glycoside) and left at 0° C. for 24 hrs at which time the reaction was complete by tlc. The reaction mixture was added to ice water (200 mL) and $CHCl_3$ (200 mL). The organic layer was removed and the aqueous solution was extracted with $CHCl_3$ (5×50 mL). The pooled organic extract was washed with ice water (200 mL), then sodium bicarbonate solution (200 mL) after which the aqueous layer remained basic, then with water (50 mL). The organic layer was dried over $MgSO_4$, filtered, and the solvent removed in vacuo to give a colorless gum. Toluene (3×100 mL) was added during the removal of solvent to azeotropically remove any remaining pyridine. The product was a mixture of peracetylated α- and β-galactosyl fluorides. These were separated by column chromatography (120 g silica gel, 5 cm column diam., 30% ethyl acetate/70% hexanes). Column fractions containing only 2,3,4,6-tetra-O-acetyl α-D-galactosyl fluoride were pooled and solvent was removed in vacuo to yield a clear oil. $^{1}H$ nmr ($CDCl_3$): δ 5.82 (dd, 1H, $J_{1,F}$ 53.0 Hz, $J_{1,2}$ 2.8 Hz, H-1), 5.55 (dd, 1H, $J_{4,5}$ 1.8 Hz, $J_{3,4}$ 2.3 Hz, H-4), 5.50 (dd, 1H, $J_{3,4}$ 2.3 Hz, $J_{2,3}$ 10.0 Hz, H-3), 5.27 (ddd, 1H, $J_{2,F}$ 21.8 Hz, $J_{2,3}$ 10.0 Hz, $J_{1,2}$ 2.8 Hz, H-2), 4.34 (td, 1H, $J_{4,5}$ 1.8 Hz, $J_{5,6}$ 5.1 Hz, $J_{5,6'}$ 7.3 H-5), 4.10 (m, 2H, H-6, H-6'), 1.97, 2.25, 2.40, 2.50 (4s, 12H, OAc). $^{19}F$ nmr ($CDCl_3$, decoupled): δ-74.74 (s, α-fluoride).

1.3 Preparation of α-D-galactosyl fluoride

The acetylated compound from above (0.428 g) was deacetylated with sodium methoxide/methanol then neutralized by passing over a silica plug using dry methanol. The solvent was removed in vacuo to give a clear oil. This was freeze-dried to a white solid (0.221 g) in 95% yield which was pure by tlc.

Example 2

This example illustrates the synthesis of a fluorescently labeled oligosaccharide using α-galactosyl fluoride.

Into an eppendorf vial were added 3 μL of 115 mM α-galactosyl fluoride (0.35 μmoles), 3 μL of 100 mM UDP (0.3 μmoles), 5 μL of 5 mM acceptor (0.025 μmoles, FCHASE-galactose=system #1 or FITC-lactose=system #2), and 4 μL of 500 mM HEPES buffer (pH 7.5) containing 50 mM $MnCl_2$ and 25 mM DTT. The reaction was initiated by the addition of 5 μL of stock α-galactosyl transferase (lgtC-18, 6 mg/mL). Reactions were run concurrently as both positive (containing 6 μL of 3.5 mM UDP-galactose instead of α-galactosyl fluoride and UDP) and negative (containing either UDP-galactose or α-galactosyl fluoride and UDP but no enzyme) controls. The course of the reaction was monitored by TLC (solvent system 7:2:1:0.1 ethyl acetate, methanol, water, acetic acid). After 1 hr, the positive control reaction for both systems was 95% completed but that of the test reaction was only about 20% or 10% completed for system #1 and #2, respectively. The reactions were left at room temperature for 17.5 hrs and then were checked by TLC. At this time, both test reactions appeared to be complete. The $R_f$ values for each of the reaction components were as follows: FCHASE-galactose acceptor $R_f$=0.6, FCHASE-lactose product $R_f$=0.5, FITC-lactose acceptor $R_f$=0.4, FITC-trisaccharide product $R_f$=0.25, α-galactosyl fluoride donor $R_f$=0.37. The plates were read using longwave UV light to visualize the fluorescent-labeled compounds and then dipped in 5% sulfuric acid in methanol and charred to observe the position of the α-galactosyl fluoride. The reaction products were isolated (Sep Pack™ $^{18}$C cartridge, washed with 10 mL water, eluted in 2 mL 50% acetonitrile) and analyzed by electrospray mass spectroscopy. m/z (amu) of products were as follows: system #1—FCHASE-galactose standard, 743.2; (−) control reaction using UDP-galactose donor, 743.2; (−) control reaction using α-galactosyl fluoride donor, 743.2; (+) control reaction using UDP-galactose donor, 905.4; test reaction using α-galactosyl fluoride donor, 905.4. system #2—FITC-lactose standard, 823.2; (−) control reaction using UDP-galactose donor, 823.2; (−) control reaction using α-galactosyl fluoride donor, 823.2; (+) control reaction using UDP-galactose donor, 985.2; test reaction using α-galactosyl fluoride donor, 985.2.

Example 3

This example illustrates that galactosyl fluoride can act as a glycosyl donor and acceptor.

It is possible that in the absence of an added acceptor substrate, the glycosyl transferase can generate Gal α(1→4) galactosyl fluoride by using α-galactosyl fluoride as both a glycosyl donor and acceptor.

To determine that the enzyme is capable of using galactosyl fluoride in the capacity of an acceptor, the following experiment was performed. Into three vials were placed 400 mM α-galactosyl fluoride, 3 mM UDP, 5 mM DTT, 15 Mm $MnCl_2$, and 100 mM Tris buffer (pH 7.5). The first vial served as a negative control and 50 mM lactose was added. The enzyme lgtC-19 (0.8 mg) was added to the second vial. The third vial served as a positive control, containing both lgtC-19 and lactose. If α-galactosyl fluoride were to act as an acceptor, the transfer product would be the disaccharide, Galα(1→4)Gal-F. After 22 hours, the reaction mixtures were analyzed by TLC and evidence for the formation of disaccharide from α-galactosyl fluoride was obtained and are tabulated in Table 1.

TABLE 1

TLC results of lgtC-19-catalyzed transfer reactions. Determined in 4:2:1:0.1 (ethyl acetate/methanol/water/acetic acid) 22 hours after initiation. (✓ indicates the component is present; X indicates the component is absent.)

| Rf (reaction component) | (+) Control | (−) Control | Test Reaction |
|---|---|---|---|
| 0.57 (α-galactosyl fluoride) | ✓ | ✓ | ✓ |
| 0.48 (Gal-Gal-F) | X | X | ✓ |
| 0.45 (Galactose) | ✓ | ✓ | ✓ |
| 0.38 (Disaccharide) | ✓ | ✓ | ✓ |
| 0.32 (Trisaccharide) | ✓ | X | ✓ |

This experiment suggests that the enzyme is capable of using α-galactosyl fluoride as both a glycosyl donor and acceptor. The product is Galα(1→4)Gal-F as shown in the test reaction with an Rf of 0.48 (Table 1).

Figure 5:
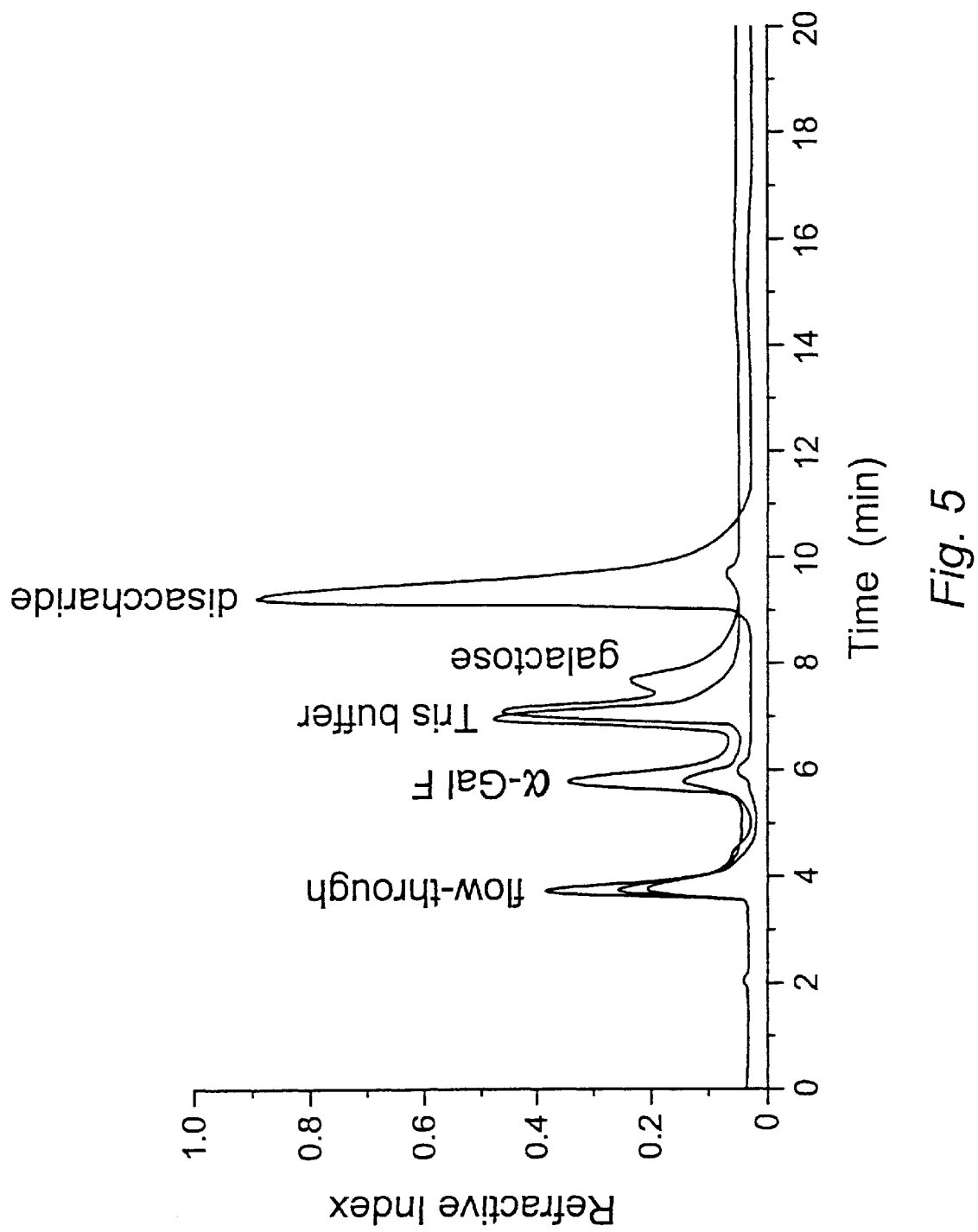
FIG. 5 shows HPLC evidence for the formation of the disaccharide by lgtC-19 using galactosyl fluoride as both a donor and an acceptor substrate.

In order to confirm that the enzyme is capable of using α-galactosyl fluoride as both a glycosyl donor and acceptor, a new reaction mixture was assembled and after 11 minutes, the reaction was stopped by immersion in a boiling water bath. This promoted hydrolysis of any glycosyl fluorides. This time the reaction mixtures were subjected to HPLC analysis. When HPLC tracings from before and after heat treatment were compared, a new disaccharide peak ($T_R$≈9.5 min) appeared, indicating that Galα(1→4)Gal-F is the initial disaccharide product formed (see, FIG. 5).

Having determined that a-galactosyl fluoride was capable of acting as both a donor and acceptor in the galactosyl transfer catalyzed by lgtC-19, the $k_{cat}/K_m$ was determined from the slope of the line tangent to the initial part of the curve described by $v_o$ versus α-galactosyl fluoride concentration. The kinetic constants for α-galactosyl fluoride and UDP are shown in Table 2.

TABLE 2

Kinetic constants obtained using α-galactosyl fluoride as the donor substrate for lgtC-19-catalyzed galactosyl transfer to lactose measured at pH 7.5 with 100 mM lactose and 15 mM $MnCl_2$, 30° C.

| Substrate | $K_{m.app}$(mM) | $k_{cat.app}$ (min$^{-1}$) | $k_{cat}K_m$ (min$^{-1}$/mM$^{-1}$) |
|---|---|---|---|
| α-galactosyl fluoride$^a$ | 220$^c$ | 1.3 | 6.0 × 10$^{-3}$ |
| UDP$^b$ | 0.41 | 1.3 | 3.2 |

$^a$determined at 2 mM UDP.
$^b$determined at 107 mM α-Galactosyl fluoride.
$^c$calculated based on the $k_{cat}$ determined for UDP.

The dependence of reaction rate upon UDP concentrations followed Michaelis-Menten kinetics, allowing apparent values of both $k_{cat}$ and $K_m$ for UDP to be determined. An estimate of $K_m$ can be made by assuming that $k_{cat}$=1.3 min$^{-1}$ (the apparent value observed under these conditions when the concentration of α-galactosyl fluoride remained fixed at 107 mM). Using this value and the measured $k_{cat}/K_{m.app}$ of 6.0×10$^{-3}$ min$^{-1}$ mM$^{-1}$ a $K_{m.app}$ of 220 mM was calculated for α-galactosyl fluoride. Although this estimate of the $K_{m.app}$ for α-galactosyl fluoride may be slightly lower than the actual value of this kinetic constant, it should provide a reasonable estimate of the true value (within a factor of two). This determination can not be made directly from the experimental data due to the large error associated with Vmax in those results. Additionally, it is important to notice that UDP need only be available to the reaction in small amounts and that its function is catalytic in nature. UDP is not consumed by the reaction.

Example 4

This example illustrates that α-galactosyl fluoride transfers its sugar residue to UDP itself, forming UDP-galactose in situ.

A Continuous Coupled Assay for UDP-Galactose Detection

Figure 6:
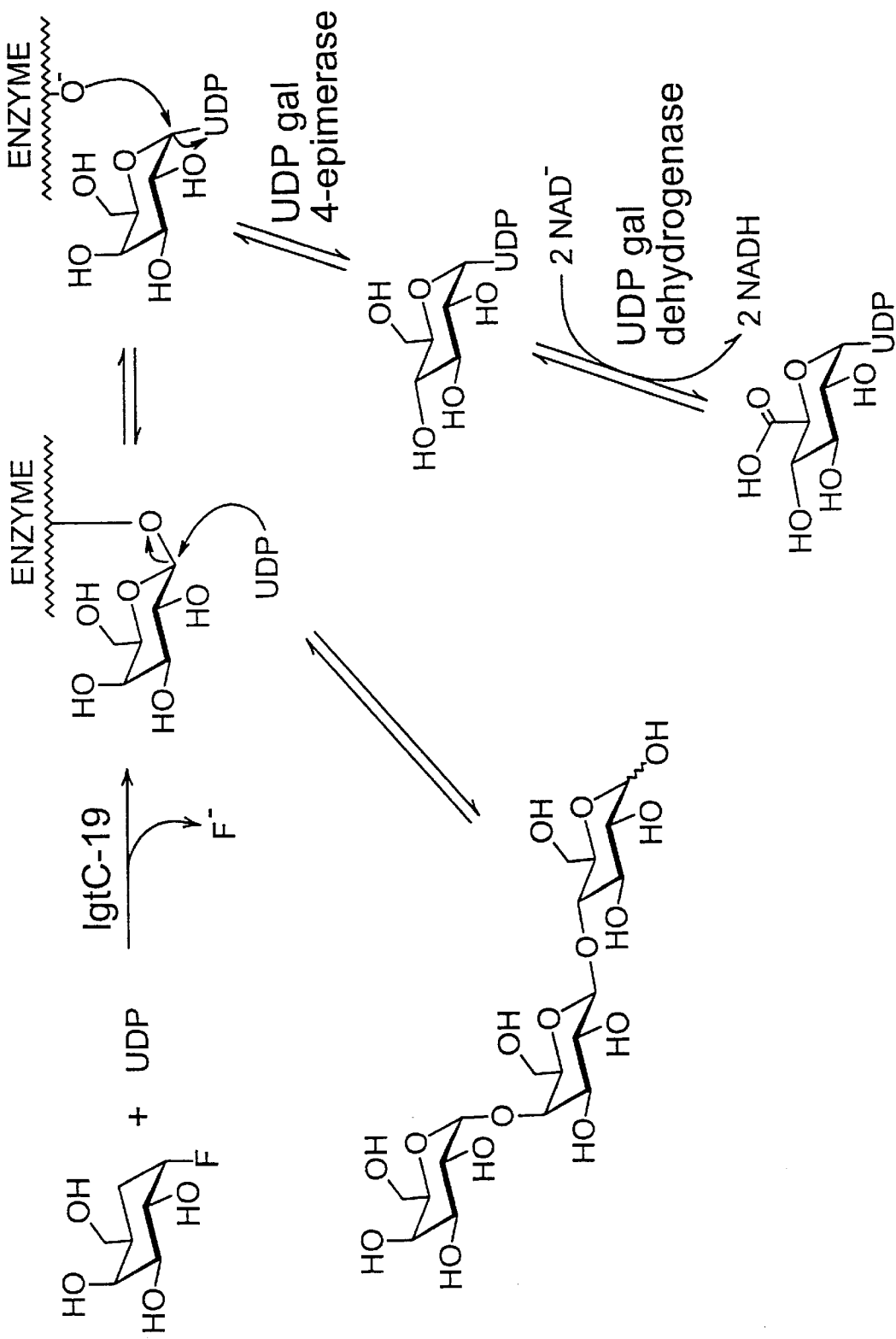
FIG. 6 shows the mechanism for the UDP-galactose 4-epimerase:UPD-glucose dehydrogenase coupling reaction.

A continuous coupled assay was developed to measure any UDP-galactose formed from α-galactosyl fluoride and UDP in the presence of the enzyme lgtC-19. This system involved two coupling enzymes: UDP-galactose 4-epimerase and UDP-glucose dehydrogenase (see, FIG. 6).

The following equilibrium is expected to form: α-galactosyl fluoride+UDP+↔UDP-galactose+E+F⁻ (where E=lgtC-19). As the natural substrate for lgtC-19, UDP-galactose binds tightly to the enzyme. Thus, strong product (UDP-galactose) inhibition would be expected to stop this reaction from proceeding very far. The coupled assay system described herein alleviates this by consuming UDP-galactose as it is released from lgtC-19. As UDP glucose formed from UDP-gal-4-epimerase is converted to UDP-glucuronic acid, a change in absorbance is measured at 340 nm that corresponds to the reaction rate, with 2 moles of NAD converted to NADH for every mole of UDP-galactose that forms. In this way, the rate of UDP-galactose production can be measured.

α-Galactosyl fluoride and UDP together serve as a UDP-galactose analogue for the galactosyl transfer reaction catalyzed by lgtC-19. Thus, it is possible that the coupling enzymes, UDP-galactose 4-epimerase and UDP-glucose dehydrogenase, might also utilize these substrates. To ensure this was not possible, a control reaction was assembled into which all assay components except lgtC-19 were added. This reaction mixture showed no appreciable absorbance change (340 nm) over a 10 minute period. Addition of UDP-galactose (0.04 mM) to the assay mix produced a sharp increase in absorbance ($\Delta A_{340} \approx 0.5$) that was directly attributed to the added substrate. Thus, the coupling system was functioning but did not utilize α-galactosyl fluoride and UDP as substrates.

Figure 7:
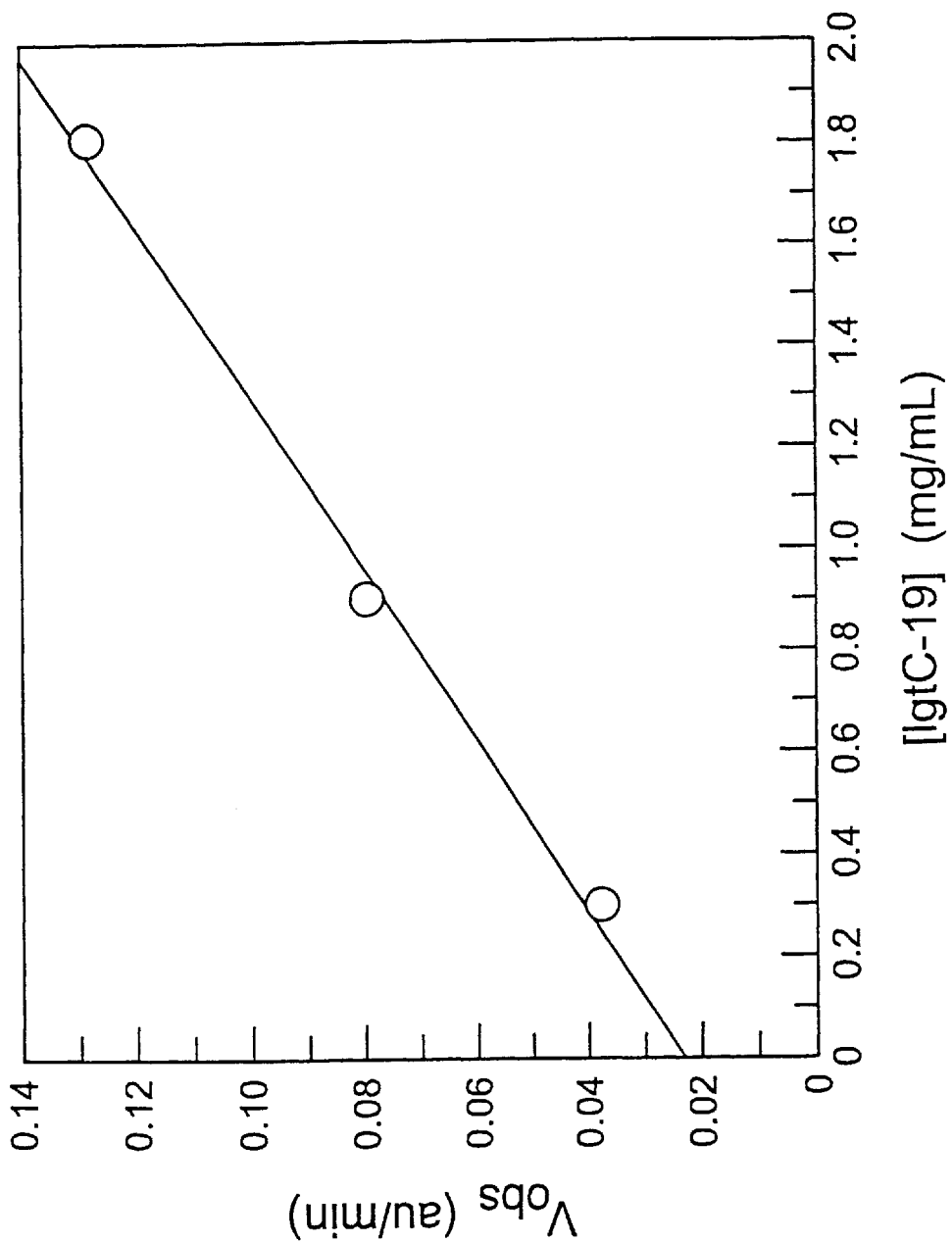
FIG. 7 shows a linear correlation between $\Delta\Delta A_{340}$ ($V_{obs}$) and IgtC-19 concentration for the UDP-galactose 4-epimerase: UDP-glucose dehydrogenase assay.

Next, the effect of varying concentrations of added lgtC-19 was determined. As shown in FIG. 7, a linear correlation was seen between the rate of absorbance change at 340 nm and the amount of lgtC-19 added to the assay mixture. This indicated that UDP-galactose is produced by the lgtC-19-catalyzed transfer of galactose from α-galactosyl fluoride to UDP and that the UDP-galactose 4-epimerase/UDP-glucose dehydrogenase coupling system was able to accurately measure the rate of the reaction.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A composition for forming a glycosylated acceptor comprising an admixture of an activated glycoside derivative, a glycosyl transferase altered by mutation, an acceptor substrate, and a catalytic amount of a nucleotide phosphate or a nucleotide phosphate analog.

2. A composition in accordance with claim 1, wherein said glycosyl transferase is a galactosyl transferase, said activated glycoside derivative is α-D-galactosyl fluoride and said acceptor substrate is a disaccharide.

3. A composition in accordance with claim 1, wherein said glycosyl transferase is a galactosyl transferase, said activated glycoside derivative is α-D-galactosyl fluoride and said acceptor substrate is lactose.

4. A composition for forming a glycosylated acceptor comprising an admixture of an activated glycoside derivative, a glycosyl transferase, a nucleotide phoshate sugar-dependent enzyme, an acceptor substrate and a member selected from the group consisting of a nucleotide phosphate and a nucleotide phosphate analog.

5. A composition in accordance with claim 4, wherein said glycosyl transferase is a galactosyl transferase, said activated glycoside derivative is α-D-galactosyl fluoride and said acceptor substrate is a disaccharide.

6. A composition in accordance with claim 4, wherein said glycosyl transferase is a galactosyl transferase, said activated glycoside derivative is α-D-galactosyl fluoride and said acceptor substrate is lactose.

7. A process for making a glycosylated acceptor, said process comprising:
admixing in an aqueous medium an activated glycoside derivative, an acceptor substrate, a glycosyl transferase, and a catalytic amount of a member selected from the group consisting of a nucleotide phosphate and a nucleotide phosphate analog, to form said glycosylated acceptor.

8. A process in accordance with claim 7, wherein said aqueous medium has a pH value of about 5 to about 10 and a temperature of about 0° C. to about 40° C.

9. A process in accordance with claim 7, wherein said activated glycoside derivative is a glycosyl fluoride.

10. A process in accordance with claim 7, wherein said activated glycoside derivative is a glycosyl mesylate.

11. A process in accordance with claim 7, further comprising the step of recovering said glycosylated acceptor.

12. A process in accordance with claim 7, wherein said glycosyl transferase is a member selected from the group consisting of α-sialyl transferases, α-glucosyl transferases, α-galactosyl transferases, α-fucosyl transferases, α-mannosyl transferases, α-xylosyl transferases, α-N-acetyl hexosaminyl transferases, β-sialyl transferases, β-glucosyl transferases, β-galactosyl transferases, β-fucosyl transferases, β-mannosyl transferases, β-xylosyl transferases, and β-N-acetyl hexosaminyl transferases.

13. A process in accordance with claim 7, wherein said aqueous medium is a buffered aqueous medium.

14. A process in accordance with claim 7, wherein said acceptor substrate is selected from the group consisting of an oligosaccharide, a monosaccharide, a fluorescent-labeled saccharide and a saccharide derivative.

15. A process in accordance with claim 14, wherein said saccharide derivative is an aminoglycoside antibiotic.

16. A process in accordance with claim 14, wherein said oligosaccharide is lactose.

17. A process in accordance with claim 14, wherein said fluorescent-labeled saccharide is selected from the group consisting of an FITC-lactose, FCHASE-lactose, FITC-galactose and FCHASE-galactose.

18. A process in accordance with claim 7, wherein said activated glycoside derivative is a member selected from the group consisting of α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride.

19. A process in accordance with claim 7, wherein said glycosyl transferase is a member selected from the group consisting of α-sialyl transferases, α-glucosyl transferases, α-galactosyl transferases, α-mannosyl transferases, α-fucosyl transferases, α-xylosyl transferases, α-N-acetyl hexosaminyl transferases, β-sialyl transferases, β-glucosyl transferases, β-galactosyl transferases, and β-N-acetyl hexosaminyl transferases.

20. A process in accordance with claim 7, wherein said glycosyl transferase is immobilized on a solid support.

21. A process in accordance with claim 7, wherein said glycosyl transferase is a galactosyl transferase, said activated glycoside derivative is α-D-galactosyl fluoride and said acceptor substrate is a disaccharide.

22. A process in accordance with claim 7, wherein said glycosyl transferase is a galactosyl transferase, said activated glycoside derivative is α-D-galactosyl fluoride and said acceptor substrate is lactose.

23. A process for forming a glycosylated acceptor by making a nucleotide phosphate glycoside in situ in a steady state concentration, said process comprising:
admixing in an aqueous medium an activated glycoside derivative, a glycosyl transferase, a member selected from the group consisting of a nucleotide phosphate and a nucleotide phosphate analog, a nucleotide phosphate sugar-dependent enzyme and at least one acceptor substrate to form a nucleotide phosphate glycoside in situ which reacts in the aqueous medium with said acceptor substrate to form said glycosylated acceptor.

24. A process for forming a glycosylated acceptor by making a nucleotide phosphate glycoside in situ in accordance with claim 23, wherein said nucleotide phosphate sugar-dependent enzyme is selected from the group consisting of a glycosyl transferase different from the glycosyl transferase in claim 23, an epimerase, a dehydrogenase, a pyrophosphorylase and a nucleotide diphosphate ribosyl transferase.

25. A process for forming a glycosylated acceptor by making a nucleotide phosphate glycoside in situ in accordance with claim 23, wherein said at least one acceptor substrate is a member selected from the group consisting of nicotinamide adenine dinucleotide, nicotinamide adenine dinucleotide phosphate, glucose, a glucoside, galactose, a galactoside, mannose, a mannoside, fucose, a fucoside, N-acetylneuraminic acid, an N-acetylneuraminide, xylose, a xyloside, N-acetylglucosamine, an N-acetylglucosaminide, N-acetylgalacotosamine, an N-acetylgalactosaminide, arabinose, an arabinoside, an antibiotic aglycone, a detergent aglycone, a lipid, a sapogenin, an oligosaccharide, a monosaccharide, a fluorescent-labeled saccharide and a saccharide derivative.

26. A process for forming a glycosylated acceptor by making a nucleotide phosphate glycoside in situ in accordance with claim 23, wherein said nucleotide phosphate glycoside does not inhibit said glycosyl transferase.

27. A process in accordance with claim 23, wherein said aqueous medium has a pH value of about 5 to about 10 and a temperature of about 0° C. to about 40° C.

28. A process in accordance with claim 23, wherein said activated glycoside derivative is a glycosyl fluoride.

29. A process in accordance with claim 23, wherein said activated glycoside derivative is a glycosyl mesylate.

30. A process in accordance with claim 23, further comprising the step of recovering said glycosylated acceptor.

31. A process in accordance with claim 23, wherein said glycosyl transferase is a member selected from the group consisting of α-sialyl transferases, α-glucosyl transferases, α-galactosyl transferases, α-fucosyl transferases, α-mannosyl transferases, α-xylosyl transferases, α-N-acetyl hexosaminyl transferases, β-sialyl transferases, β-glucosyl transferases, β-galactosyl transferases, β-fucosyl transferases, β-mannosyl transferases, β-xylosyl transferases, and β-N-acetyl hexosaminyl transferases.

32. A process in accordance with claim 23, wherein said nucleotide phosphate sugar-dependent enzyme is a glycosyl transferase different from the glycosyl transferase in claim 23 selected from the group consisting of α-sialyl transferases, α-glucosyl transferases, α-galactosyl transferases, α-fucosyl transferases, α-mannosyl transferases, α-xylosyl transferases, α-N-acetyl hexosaminyl transferases, β-sialyl transferases, β-glucosyl transferases, β-galactosyl transferases, β-fucosyl transferases, β-mannosyl transferases, β-xylosyl transferases, and β-N-acetyl hexosaminyl transferases.

33. A process in accordance with claim 23, wherein said aqueous medium is a buffered aqueous medium.

34. A process in accordance with claim 25, wherein said saccharide derivative is an aminoglycoside antibiotic.

35. A process in accordance with claim 25, wherein said oligosaccharide is lactose.

36. A process in accordance with claim 25, wherein said fluorescent-labeled saccharide is selected from the group consisting of an FITC-lactose, FCHASE-lactose, FITC-galactose and FCHASE-galactose.

37. A process in accordance with claim 23, wherein said activated glycoside derivative is a member selected from the group consisting of α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosyl fluoride.

38. A process in accordance with claim 23, wherein said glycosyl transferase is immobilized on a solid support.

39. A process in accordance with claim 23, wherein said glycosyl transferase is a galactosyl transferase and said activated glycoside derivative is α-D-galactosyl fluoride.

* * * * *